(12) United States Patent
Soff et al.

(10) Patent No.: US 6,576,609 B1
(45) Date of Patent: Jun. 10, 2003

US006576609B1

(54) METHODS AND COMPOSITIONS FOR GENERATING ANGIOSTATIN

(75) Inventors: Gerald Soff, Skokie, IL (US); Stephen T. Gately, Palatine, IL (US); Przemyslaw Twardowski, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 08/991,761

(22) Filed: Dec. 16, 1997

Related U.S. Application Data

(63) Continuation-in-part of application No. 08/710,305, filed on Sep. 17, 1996, now Pat. No. 5,808,012, and a continuation of application No. PCT/US97/16539, filed on Sep. 17, 1997.

(51) Int. Cl.$^7$ .............................................. A61K 38/00
(52) U.S. Cl. ...................... 514/12; 435/217; 530/350; 530/380
(58) Field of Search .......................... 514/12; 435/217; 530/350, 380

(56) References Cited

U.S. PATENT DOCUMENTS

| | | | | |
|---|---|---|---|---|
| 4,011,142 A | * | 3/1977 | Jacobi ..................... | 195/103.5 |
| 4,968,494 A | * | 11/1990 | Claremon et al. ........ | 424/94.64 |
| 5,021,404 A | | 6/1991 | Folkman et al. ............... | 514/26 |
| 5,135,919 A | | 8/1992 | Folkman et al. ............... | 514/56 |
| 5,290,807 A | | 3/1994 | Folkman et al. ............. | 514/475 |
| 5,504,074 A | | 4/1996 | D'Amato et al. ........... | 514/182 |
| 5,639,725 A | * | 6/1997 | O'Reilly et al. .............. | 514/12 |
| 5,698,586 A | | 12/1997 | Kishimoto et al. .......... | 514/475 |
| 5,733,876 A | | 3/1998 | O'Reilly et al. .............. | 514/12 |
| 5,776,704 A | | 7/1998 | O'Reilly et al. ............ | 435/7.21 |
| 5,792,845 A | | 8/1998 | O'Reilly et al. ........... | 536/23.1 |
| 5,837,682 A | | 11/1998 | Folkman et al. .............. | 514/12 |
| 5,854,221 A | | 12/1998 | Cao et al. ...................... | 514/12 |
| 5,861,372 A | | 1/1999 | Folkman et al. ................ | 514/2 |
| 5,885,795 A | | 3/1999 | O'Reilly et al. ............ | 435/69.1 |
| 5,888,967 A | * | 3/1999 | Honold et al. .................. | 514/7 |
| 6,024,688 A | | 2/2000 | Folkman et al. .............. | 574/12 |

FOREIGN PATENT DOCUMENTS

| | | |
|---|---|---|
| WO | WO 90/12580 | 11/1990 |
| WO | WO 91/10424 | 7/1991 |
| WO | PCT WO 95/29242 | 11/1995 |
| WO | WO 96/35774 | 11/1996 |
| WO | WO 96/41194 | 12/1996 |
| WO | WO 97/15666 | 5/1997 |
| WO | WO 97/23500 | 7/1997 |
| WO | WO 97/41824 | 11/1997 |
| WO | WO 98/54217 | 12/1998 |
| WO | WO 99/00420 | 1/1999 |

OTHER PUBLICATIONS

1/ Koch, AE et al. Aents Action 34(3–4) :350–7, 1991.*
3/ Gately et al. Cancer Res. 56: 4887–4890, 1996.*
4/ Maloau, W et al. Aido Res. Human Retrovirus, 14 (17): 1589–1596, 1998.*
Devlin, TM—Text book of Modern, p. 483, 1982.*
1/ Meehan, Blood Coagulation & Fibroinolysis, 6: 105–112, 1995.*
2/ Gonzalez–Lois, C. Archives Path. Lab. Med. 125 (6): 796–8, 2001.*
3/ Albiui, A. Intl. J. Cancer, 61(1): 121–9, 1995.*
4/ Tsuji, A et al. Clin. Exp. Immunol. 93(3): 308–12, 1993.*
5/ Calbo, FA, Cancer, 70 (11): 2624–2630, 1992.*
Volpert et al, Captopril Inhibits Angiogenesis and Slows the Growth of Experimental Tumors in Rats. J. Clin. Invest. 98(3): 671–679 (Aug. 1996).
Lannutti et al., Cancer Research 57: 5277–5280 (Dec. 1, 1997).
Engleka, KA, 1992, J. Biol Chem 267(16): 11307–15.
O'Reilly et al. Cold. Spr. Harb Symp. Quant. Biol. 59:471–482, 1994.
Ashino–Fuse et al., *Int. J. Cancer*, 44:859–864 (1989).
Bell, *Semin. Thromb. Hemost.*, 12:459–478 (1996).
Berman et al., *Invest. Opthalmol. Vis. Sci*, 22:191–199 (1982).
Bianchi et al., *Cancer Research*, 54:861–866 (1994).
Blei et al., *J. Cell. Physiol.*, 155:568–578 (1993).
Goldfarb et al., *Seminars Thromb. Hemostat.*, 12(4):337–338 (1986).
Lu et al., *FEBS Let.*, 356:56–59 (1994).
Mandriota et al., *J. Biol. Chem.*, 270(17):9709–9716 (1995).
Mignatti et al., *J. Cell Biol.*, 113(5):1193–1201 (1991).
Min et al., *Cancer Res.*, 56:2428–2433 (1996).
Montesano et al., *Proc. Natl. Acad. Sci.*, 83:7297–7301 (1986).
Rifkin et al., *Acta Biol. Med. Germ.*, 40:1259–1263 (1981).
Soff et al., *J. Clin. Invest.*, 96:2593–2600 (1995).
Sueishi et al., *Ann. NY Acad. Sci*, 598:223–231 (1990).
Yasunaga et al., *Laboratory Investigation*, 61(6):698–704 (1989).
Arrigoni–Martelli, et al., *Eur. J. Rheumatol. Inflamm.*, 1:197–203 (1978).

(List continued on next page.)

*Primary Examiner*—Susan Ungar
*Assistant Examiner*—Minh-Tam Davis
(74) *Attorney, Agent, or Firm*—Pennie & Edmonds LLP

(57) ABSTRACT

The invention provides a method of treating a neoplastic disease in a human by administering a therapeutically effective amount of plasminogen activator effective to increase the amount of angiostatin present in the human to treat the disease. The invention also provides a method of treating a neoplastic disease in a human by administering a therapeutically effective amount of plasminogen activator and sulfhydryl donor effective to increase the amount of angiostatin present in the human to treat said disease.

14 Claims, 13 Drawing Sheets

OTHER PUBLICATIONS

Dong et al., *Cell*, 88:801–810 (1997).
Jellum et al., *Scand. J. Rheumatology*, 28(supp):28–36 (1979).
Jellum et al., *Annals of the Rheumatic Diseases*, 39:155–158 (1980).
Jellum et al., *Annals of the Rheumatic Diseases*, 41:431–432 (1982).
Munthe et al., "Tolerance and Effectiveness of Sodium Thiomalate Without Cold in Rheumatoid Arthritis" XVII Nordic Congress of Rheumatology in Helsinger, 1978, p. 21, abstract #42.
Munthe et al., *Scand. J. Rheumatology*, 28(supp):6–12 (1979).
Munthe et al., *J. Rheumatol*, 8(supp 7):14–19 (1981).
Battegay, 1995, *J. Mol. Med.*, 73:333–346.
Brem et al., 1990, *American Journal of Pathology*, 137(5):1121–1142.
Brem, et al., 1995, *Lancet*, 345:1008–1012.
Castellino & Powell, 1981, *Methods Enzymol*, 80:365–78.
Chen et al., 1995, *Cancer Research*, 55:4230–4233.
Dameron et al., 1994, *Science*, 265:1582–1584.
Dong et al., 1996, *Proc. Am. Assoc. Cancer Res.*, 37:58.
Folkman & Shing, 1992, *J. Biol. Chem*, 267:10931–10934.
Heussen & Dowdle, 1980, *Anal. Biochem.*, 102:196–202.
Hourani et al., 1969, *Laboratory Investigation*, 21(5):434–438.
Laemmli, 1970, *Nature*, 227:680–685.
Littman et al., 1963, *P.S.E.B.M.*, 113:667–674.
Matsubara et al., 1989, *J. Clin. Invest.*, 83:158–167.
O'Reilly et al., 1996, *Nature Med.* 2:689–692.
O'Reilly et al., 1994, *Cell*, 79:315–328.
Polverini et al., 1991, *Methods Enzymol*, 198:440–450.
Schnaper et al., 1993, *J. Cell. Physiol*, 156:235–246.
Sottrup–Jensen et al., 1978, *Progress in Chemical Fibrinolysis and Thrombolysis*, 3:191–209.
Takano et al., 1994, *Cancer Res.*, 54:2654–2660.
Cao et al., 1997, *J. Biol. Chem.*, 272(36):22924–22928.
Gately et al., 1996, *Cancer Res.*, 56:4887–4890.
Mooser et al., 1996, *J. Clin. Invest.*, 97(3):858–864.
Stathakis et al., 1997, *J. Biol. Chem.*, 272(33):20641–20645.

* cited by examiner

FIG.5A
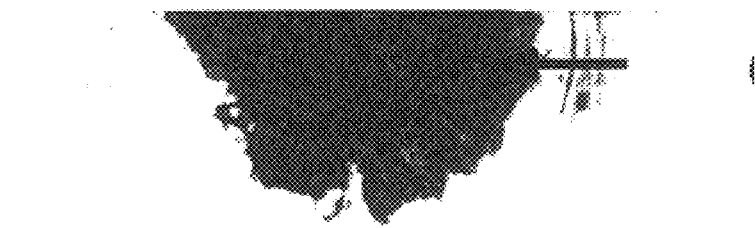
FIG.5B

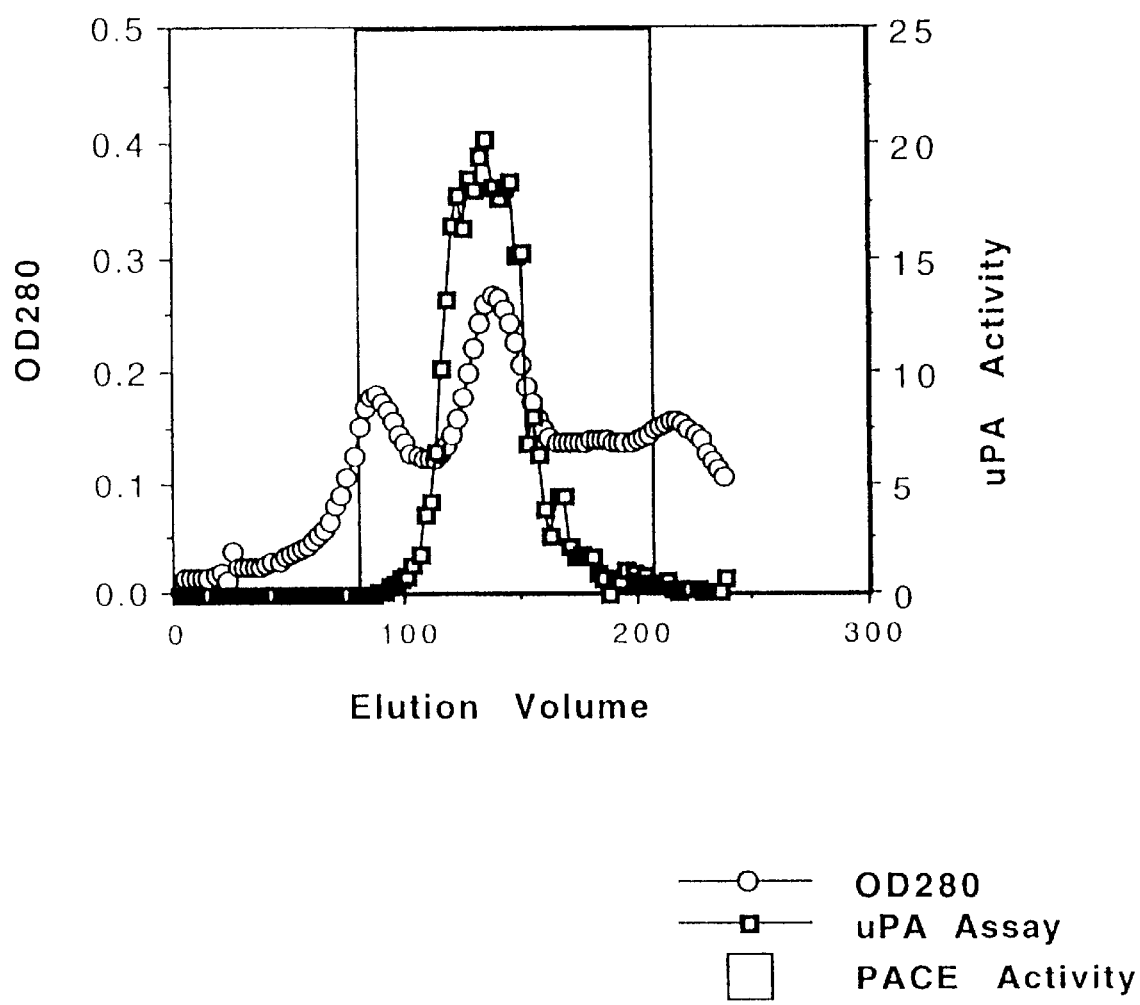

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Lys Val Tyr Leu Ser Glu Cys Lys Thr Gly
1            5                 10

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

Lys Leu Tyr Asp Tyr Cys Asp Val
1            5

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Leu Tyr Asp Tyr Cys Asp Val
1               5
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Cys Tyr Thr Thr Asn Pro Arg
1               5
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Cys Tyr Thr Thr Asn Pro Arg Lys
1               5
```

(2) INFORMATION FOR SEQ ID NO:6:

(i) SEQUENCE CHARACTERISTICS:
        (A) LENGTH: 791 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
                20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
        50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95
```

```
Ser Lys Thr Lys Asn Gly Ile Thr Cys Gln Lys Trp Ser Ser Thr Ser
            100                 105                 110
Pro His Arg Pro Arg Phe Ser Pro Ala Thr His Pro Ser Glu Gly Leu
            115                 120                 125
Glu Glu Asn Tyr Cys Arg Asn Pro Asp Asn Asp Pro Gln Gly Pro Trp
            130                 135                 140
Cys Tyr Thr Thr Asp Pro Glu Lys Arg Tyr Asp Tyr Cys Asp Ile Leu
145                 150                 155                 160
Glu Cys Glu Glu Glu Cys Met His Cys Ser Gly Glu Asn Tyr Asp Gly
                165                 170                 175
Lys Ile Ser Lys Thr Met Ser Gly Leu Glu Cys Gln Ala Trp Asp Ser
            180                 185                 190
Gln Ser Pro His Ala His Gly Tyr Ile Pro Ser Lys Phe Pro Asn Lys
            195                 200                 205
Asn Leu Lys Lys Asn Tyr Cys Arg Asn Pro Asp Arg Glu Leu Arg Pro
            210                 215                 220
Trp Cys Phe Thr Thr Asp Pro Asn Lys Arg Trp Glu Leu Cys Asp Ile
225                 230                 235                 240
Pro Arg Cys Thr Thr Pro Pro Ser Ser Gly Pro Thr Tyr Gln Cys
                245                 250                 255
Leu Lys Gly Thr Gly Glu Asn Tyr Arg Gly Asn Val Ala Val Thr Val
                260                 265                 270
Ser Gly His Thr Cys Gln His Trp Ser Ala Gln Thr Pro His Thr His
            275                 280                 285
Asn Arg Thr Pro Glu Asn Phe Pro Cys Lys Asn Leu Asp Glu Asn Tyr
            290                 295                 300
Cys Arg Asn Pro Asp Gly Lys Arg Ala Pro Trp Cys His Thr Thr Asn
305                 310                 315                 320
Ser Gln Val Arg Trp Glu Tyr Cys Lys Ile Pro Ser Cys Asp Ser Ser
                325                 330                 335
Pro Val Ser Thr Glu Gln Leu Ala Pro Thr Ala Pro Pro Glu Leu Thr
            340                 345                 350
Pro Val Val Gln Asp Cys Tyr His Gly Asp Gly Gln Ser Tyr Arg Gly
            355                 360                 365
Thr Ser Ser Thr Thr Thr Thr Gly Lys Lys Cys Gln Ser Trp Ser Ser
370                 375                 380
Met Thr Pro His Arg His Gln Lys Thr Pro Glu Asn Tyr Pro Asn Ala
385                 390                 395                 400
Gly Leu Thr Met Asn Tyr Cys Arg Asn Pro Asp Ala Asp Lys Gly Pro
            405                 410                 415
Trp Cys Phe Thr Thr Asp Pro Ser Val Arg Trp Glu Tyr Cys Asn Leu
            420                 425                 430
Lys Lys Cys Ser Gly Thr Glu Ala Ser Val Val Ala Pro Pro Val
            435                 440                 445
Val Leu Leu Pro Asp Val Glu Thr Pro Ser Glu Glu Asp Cys Met Phe
            450                 455                 460
Gly Asn Gly Lys Gly Tyr Arg Gly Lys Arg Ala Thr Thr Val Thr Gly
465                 470                 475                 480
Thr Pro Cys Gln Asp Trp Ala Ala Gln Glu Pro His Arg His Ser Ile
            485                 490                 495
Phe Thr Pro Glu Thr Asn Pro Arg Ala Gly Leu Glu Lys Asn Tyr Cys
            500                 505                 510
```

```
Arg Asn Pro Asp Gly Asp Val Gly Gly Pro Trp Cys Tyr Thr Thr Asn
    515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790
```

(2) INFORMATION FOR SEQ ID NO:7:

(i) SEQUENCE CHARACTERISTICS:
        (A) LENGTH: 812 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Leu Pro Ala Ser Pro Lys Met Glu His Lys Ala Val Val Phe Leu
1               5                   10                  15

Leu Leu Leu Phe Leu Lys Ser Gly Leu Gly Asp Leu Leu Asp Asp Tyr
            20                  25                  30

Val Asn Thr Gln Gly Ala Ser Leu Leu Ser Leu Ser Arg Lys Asn Leu
        35                  40                  45

Ala Gly Arg Ser Val Glu Asp Cys Ala Ala Lys Cys Glu Glu Glu Thr
    50                  55                  60
```

-continued

```
Asp Phe Val Cys Arg Ala Phe Gln Tyr His Ser Lys Glu Gln Gln Cys
 65                  70                  75                  80

Val Val Met Ala Glu Asn Ser Lys Asn Thr Pro Val Phe Arg Met Arg
                 85                  90                  95

Asp Val Ile Leu Tyr Glu Lys Arg Ile Tyr Leu Leu Glu Cys Lys Thr
            100                 105                 110

Gly Asn Gly Gln Thr Tyr Arg Gly Thr Thr Ala Glu Thr Lys Ser Gly
            115                 120                 125

Val Thr Cys Gln Lys Trp Ser Ala Thr Ser Pro His Val Pro Lys Phe
        130                 135                 140

Ser Pro Glu Lys Phe Pro Leu Ala Gly Leu Glu Glu Asn Tyr Cys Arg
145                 150                 155                 160

Asn Pro Asp Asn Asp Glu Asn Gly Pro Trp Cys Tyr Thr Thr Asp Pro
                165                 170                 175

Asp Lys Arg Tyr Asp Tyr Cys Asp Ile Pro Glu Cys Glu Asp Lys Cys
            180                 185                 190

Met His Cys Ser Gly Glu Asn Tyr Glu Gly Lys Ile Ala Lys Thr Met
            195                 200                 205

Ser Gly Arg Asp Cys Gln Ala Trp Asp Ser Gln Ser Pro His Ala His
        210                 215                 220

Gly Tyr Ile Pro Ser Lys Phe Pro Asn Lys Asn Leu Lys Met Asn Tyr
225                 230                 235                 240

Cys Arg Asn Pro Asp Gly Glu Pro Arg Pro Trp Cys Phe Thr Thr Asp
                245                 250                 255

Pro Gln Lys Arg Trp Glu Phe Cys Asp Ile Pro Arg Cys Thr Thr Pro
            260                 265                 270

Pro Pro Ser Ser Gly Pro Lys Tyr Gln Cys Leu Lys Gly Thr Gly Lys
        275                 280                 285

Asn Tyr Gly Gly Thr Val Ala Val Thr Glu Ser Gly His Thr Cys Gln
290                 295                 300

Arg Trp Ser Glu Gln Thr Pro His Lys His Asn Arg Thr Pro Glu Asn
305                 310                 315                 320

Phe Pro Cys Lys Asn Leu Glu Glu Asn Tyr Cys Arg Asn Pro Asn Gly
                325                 330                 335

Glu Lys Ala Pro Trp Cys Tyr Thr Thr Asn Ser Glu Val Arg Trp Glu
            340                 345                 350

Tyr Cys Thr Ile Pro Ser Cys Glu Ser Ser Pro Leu Ser Thr Glu Arg
        355                 360                 365

Met Asp Val Pro Val Pro Pro Glu Gln Thr Pro Val Pro Gln Asp Cys
        370                 375                 380

Tyr His Gly Asn Gly Gln Ser Tyr Arg Gly Thr Ser Ser Thr Thr Ile
385                 390                 395                 400

Thr Gly Arg Lys Cys Gln Ser Trp Ser Ser Met Thr Pro His Arg His
                405                 410                 415

Leu Lys Thr Pro Glu Asn Tyr Pro Asn Ala Gly Leu Thr Met Asn Tyr
            420                 425                 430

Cys Arg Asn Pro Asp Ala Asp Lys Ser Pro Trp Cys Tyr Thr Thr Asp
        435                 440                 445

Pro Arg Val Arg Trp Glu Phe Cys Asn Leu Lys Lys Cys Ser Glu Thr
            450                 455                 460

Pro Glu Gln Val Pro Ala Ala Pro Gln Ala Pro Gly Val Glu Asn Pro
465                 470                 475                 480

Pro Glu Ala Asp Cys Met Ile Gly Thr Gly Lys Ser Tyr Arg Gly Lys
```

```
                          485                 490                     495
Lys Ala Thr Thr Val Ala Gly Val Pro Cys Gln Glu Trp Ala Ala Gln
                    500                 505                 510

Glu Pro His Gln His Ser Ile Phe Thr Pro Glu Thr Asn Pro Gln Ser
            515                 520                 525

Gly Leu Glu Arg Asn Tyr Cys Arg Asn Pro Asp Gly Asp Val Asn Gly
        530                 535                 540

Pro Trp Cys Tyr Thr Met Asn Pro Arg Lys Pro Phe Asp Tyr Cys Asp
545                 550                 555                 560

Val Pro Gln Cys Glu Ser Ser Phe Asp Cys Gly Lys Pro Lys Val Glu
                565                 570                 575

Pro Lys Lys Cys Ser Gly Arg Ile Val Gly Gly Cys Val Ser Lys Pro
            580                 585                 590

His Ser Trp Pro Trp Gln Val Ser Leu Arg Arg Ser Ser Arg His Phe
        595                 600                 605

Cys Gly Gly Thr Leu Ile Ser Pro Lys Trp Val Leu Thr Ala Ala His
610                 615                 620

Cys Leu Asp Asn Ile Leu Ala Leu Ser Phe Tyr Lys Val Ile Leu Gly
625                 630                 635                 640

Ala His Asn Glu Lys Val Arg Glu Gln Ser Val Gln Glu Ile Pro Val
                645                 650                 655

Ser Arg Leu Phe Arg Glu Pro Ser Gln Ala Asp Ile Ala Leu Leu Lys
            660                 665                 670

Leu Ser Arg Pro Ala Ile Ile Thr Lys Glu Val Ile Pro Ala Cys Leu
        675                 680                 685

Pro Pro Pro Asn Tyr Met Val Ala Ala Arg Thr Glu Cys Tyr Ile Thr
    690                 695                 700

Gly Trp Gly Glu Thr Gln Gly Thr Phe Gly Glu Gly Leu Leu Lys Glu
705                 710                 715                 720

Ala His Leu Pro Val Ile Glu Asn Lys Val Cys Asn Arg Asn Glu Tyr
                725                 730                 735

Leu Asp Gly Arg Val Lys Pro Thr Glu Leu Cys Ala Gly His Leu Ile
            740                 745                 750

Gly Gly Thr Asp Ser Cys Gln Gly Asp Ser Gly Gly Pro Leu Val Cys
        755                 760                 765

Phe Glu Lys Asp Lys Tyr Ile Leu Gln Gly Val Thr Ser Trp Gly Leu
    770                 775                 780

Gly Cys Ala Arg Pro Asn Lys Pro Gly Val Tyr Val Arg Val Ser Pro
785                 790                 795                 800

Tyr Val Pro Trp Ile Glu Glu Thr Met Arg Arg Asn
                805                 810

(2) INFORMATION FOR SEQ ID NO:8:

(i) SEQUENCE CHARACTERISTICS:
        (A) LENGTH: 333 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Ser Asp Cys Met Phe Gly Asn Gly Lys Gly Tyr Arg Gly Lys Lys
1               5                   10                  15

Ala Thr Thr Val Met Gly Ile Pro Cys Gln Glu Trp Ala Ala Gln Glu
```

-continued

```
                20                  25                  30

Pro His Arg His Ser Ile Phe Thr Pro Glu Thr Asn Pro Gln Ala Gly
        35                  40                  45

Leu Glu Lys Asn Tyr Cys Arg Asn Pro Asp Gly Asp Val Asn Gly Pro
 50                  55                  60

Trp Cys Tyr Thr Met Asn Gln Arg Lys Leu Phe Asp Tyr Cys Asp Val
 65                  70                  75                  80

Pro Gln Cys Val Ser Thr Ser Phe Asp Cys Gly Lys Pro Gln Val Glu
                85                  90                  95

Pro Lys Lys Cys Pro Gly Arg Val Val Gly Gly Cys Val Ala Asn Pro
                100                 105                 110

His Ser Trp Pro Trp Gln Ile Ser Leu Arg Thr Arg Tyr Gly Lys His
                115                 120                 125

Phe Cys Gly Gly Thr Leu Ile Ser Pro Glu Trp Val Leu Thr Ala Ala
        130                 135                 140

His Cys Leu Glu Arg Ser Ser Arg Pro Ala Ser Tyr Lys Val Ile Leu
145                 150                 155                 160

Gly Ala His Lys Glu Val Asn Leu Glu Ser Asp Val Gln Glu Ile Glu
                165                 170                 175

Val Tyr Lys Leu Phe Leu Glu Pro Thr Arg Ala Asp Ile Ala Leu Leu
                180                 185                 190

Lys Leu Ser Ser Pro Ala Val Ile Thr Ser Lys Val Ile Pro Ala Cys
        195                 200                 205

Leu Pro Pro Asn Tyr Val Val Ala Asp Arg Thr Leu Cys Tyr Ile
        210                 215                 220

Thr Gly Trp Gly Glu Thr Gln Gly Thr Tyr Gly Ala Gly Leu Leu Lys
225                 230                 235                 240

Glu Ala Gln Leu Pro Val Ile Glu Asn Lys Val Cys Asn Arg Tyr Glu
                245                 250                 255

Tyr Leu Asn Gly Arg Val Lys Ser Thr Glu Leu Cys Ala Gly Asn Leu
                260                 265                 270

Ala Gly Gly Thr Asp Ser Cys Gln Gly Asp Ser Gly Gly Pro Leu Val
        275                 280                 285

Cys Phe Glu Lys Asp Lys Tyr Ile Leu Gln Gly Val Thr Ser Trp Gly
 290                 295                 300

Leu Gly Cys Ala Arg Pro Asn Lys Pro Gly Val Tyr Val Arg Val Ser
305                 310                 315                 320

Arg Phe Val Thr Trp Ile Glu Gly Ile Met Arg Asn Asn
                325                 330

(2) INFORMATION FOR SEQ ID NO:9:

(i) SEQUENCE CHARACTERISTICS:
        (A) LENGTH: 809 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Met Gln Arg Lys Glu Leu Val Leu Leu Phe Leu Leu Phe Leu Gln Pro
 1               5                   10                  15

Gly His Gly Ile Pro Leu Asp Asp Tyr Val Thr Thr Gln Gly Ala Ser
                20                  25                  30

Leu Cys Ser Ser Thr Lys Lys Gln Leu Ser Val Gly Ser Thr Glu Glu
```

-continued

```
                35                  40                  45
Cys Ala Val Lys Cys Glu Lys Glu Thr Ser Phe Ile Cys Arg Ser Phe
 50                  55                  60
Gln Tyr His Ser Lys Glu Gln Cys Val Ile Met Ala Glu Asn Ser
 65                  70                  75                  80
Lys Ser Thr Pro Val Leu Arg Met Arg Asp Val Ile Leu Phe Glu Lys
                 85                  90                  95
Lys Met Tyr Leu Ser Glu Cys Lys Val Gly Asn Gly Lys Tyr Tyr Arg
                100                 105                 110
Gly Thr Val Ser Lys Thr Lys Thr Gly Leu Thr Cys Gln Lys Trp Ser
                115                 120                 125
Ala Glu Thr Pro His Lys Pro Arg Phe Ser Pro Asp Glu Asn Pro Ser
130                 135                 140
Glu Gly Leu Asp Gln Asn Tyr Cys Arg Asn Pro Asp Asn Asp Pro Lys
145                 150                 155                 160
Gly Pro Trp Cys Tyr Thr Met Asp Pro Glu Val Arg Tyr Glu Tyr Cys
                165                 170                 175
Glu Ile Ile Gln Cys Glu Asp Glu Cys Met His Cys Ser Gly Gln Asn
                180                 185                 190
Tyr Val Gly Lys Ile Ser Arg Thr Met Ser Gly Leu Glu Cys Gln Pro
                195                 200                 205
Trp Asp Ser Gln Ile Pro His Pro His Gly Phe Ile Pro Ser Lys Phe
210                 215                 220
Pro Ser Lys Asn Leu Lys Met Asn Tyr Cys Arg Asn Pro Asp Gly Glu
225                 230                 235                 240
Pro Arg Pro Trp Cys Phe Thr Met Asp Arg Asn Lys Arg Trp Glu Tyr
                245                 250                 255
Cys Asp Ile Pro Arg Cys Thr Thr Pro Pro Pro Ser Gly Pro Thr
                260                 265                 270
Tyr Gln Cys Leu Met Gly Asn Gly Glu His Tyr Gln Gly Asn Val Ala
                275                 280                 285
Val Thr Val Ser Gly Leu Thr Cys Gln Arg Trp Gly Glu Gln Ser Pro
                290                 295                 300
His Arg His Asp Arg Thr Pro Glu Asn Tyr Pro Cys Lys Asn Leu Asp
305                 310                 315                 320
Glu Asn Tyr Cys Arg Asn Pro Asp Gly Glu Pro Ala Pro Trp Cys Phe
                325                 330                 335
Thr Thr Asn Ser Ser Val Arg Trp Glu Phe Cys Lys Ile Pro Asp Cys
                340                 345                 350
Val Ser Ser Ala Ser Glu Thr Glu His Ser Asp Ala Pro Val Ile Val
                355                 360                 365
Pro Pro Glu Gln Thr Pro Val Val Gln Glu Cys Tyr Gln Gly Asn Gly
370                 375                 380
Gln Thr Tyr Arg Gly Thr Ser Ser Thr Ile Thr Gly Lys Lys Cys
385                 390                 395                 400
Gln Pro Trp Thr Ser Met Arg Pro His Arg His Ser Lys Thr Pro Glu
                405                 410                 415
Asn Tyr Pro Asp Ala Asp Leu Thr Met Asn Tyr Cys Arg Asn Pro Asp
                420                 425                 430
Gly Asp Lys Gly Pro Trp Cys Tyr Thr Thr Asp Pro Ser Val Arg Trp
                435                 440                 445
Glu Phe Cys Asn Leu Lys Lys Cys Ser Gly Thr Glu Met Ser Ala Thr
450                 455                 460
```

```
Asn Ser Ser Pro Val Gln Val Ser Ser Ala Ser Glu Ser Ser Glu Gln
465                 470                 475                 480

Asp Cys Ile Ile Asp Asn Gly Lys Gly Tyr Arg Gly Thr Lys Ala Thr
            485                 490                 495

Thr Gly Ala Gly Thr Pro Cys Gln Ala Trp Ala Ala Gln Glu Pro His
        500                 505                 510

Arg His Ser Ile Phe Thr Pro Glu Thr Asn Pro Arg Ala Asp Leu Gln
        515                 520                 525

Glu Asn Tyr Cys Arg Asn Pro Asp Gly Asp Ala Asn Gly Pro Trp Cys
    530                 535                 540

Tyr Thr Thr Asn Pro Arg Lys Leu Phe Asp Tyr Cys Asp Ile Pro His
545                 550                 555                 560

Cys Val Ser Pro Ser Ser Ala Asp Cys Gly Lys Pro Lys Val Glu Pro
                565                 570                 575

Lys Lys Cys Pro Gly Arg Val Gly Gly Cys Val Ala His Pro His Ser
            580                 585                 590

Trp Pro Trp Gln Val Ser Leu Arg Arg Phe Gly Gln His Phe Cys Gly
        595                 600                 605

Gly Thr Leu Ile Ser Pro Glu Trp Val Val Thr Ala Ala His Cys Leu
        610                 615                 620

Glu Lys Phe Ser Asn Pro Ala Ile Tyr Lys Val Val Leu Gly Ala His
625                 630                 635                 640

Gln Glu Thr Arg Leu Glu Arg Asp Val Gln Ile Lys Gly Val Thr Lys
                645                 650                 655

Met Phe Leu Glu Pro Tyr Arg Ala Asp Ile Ala Leu Leu Lys Leu Ser
            660                 665                 670

Ser Pro Ala Ile Ile Thr Asp Lys Asp His Pro Ala Cys Leu Pro Asn
        675                 680                 685

Ser Asn Tyr Met Val Ala Asp Arg Ser Leu Cys Tyr Ile Thr Gly Trp
    690                 695                 700

Gly Glu Thr Lys Gly Thr Tyr Gly Ala Gly Leu Leu Lys Glu Ala Gln
705                 710                 715                 720

Leu Pro Val Ile Glu Lys Val Cys Asn Arg Gln Ser Phe Leu Asn Gly
                725                 730                 735

Arg Val Arg Ser Thr Glu Leu Cys Ala Gly His Leu Ala Gly Gly Val
            740                 745                 750

Asp Ser Cys Gln Gly Asp Ser Gly Gly Pro Leu Val Cys Phe Glu Lys
        755                 760                 765

Asp Arg Tyr Ile Leu Gln Gly Val Thr Ser Trp Gly Leu Gly Cys Ala
        770                 775                 780

Arg Leu Thr Arg Pro Gly Val Tyr Val Arg Val Ser Arg Tyr Val Ser
785                 790                 795                 800

Trp Leu Gln Asp Val Met Arg Asn Asn
                805

(2) INFORMATION FOR SEQ ID NO:10:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:
```

```
Val Gln Glu Pro Ser Glu Pro Asp Cys Met Leu Gly Ile Gly Lys Gly
1               5                  10                 15

Tyr Gln Gly Lys Lys Ala Thr Thr Val Thr Gly Thr Arg Cys Gln Ala
            20                  25                  30

Trp Ala Ala Gln Glu Pro His Arg His Ser Ile Phe Thr Pro Glu Ala
            35                  40                  45

Asn Pro Trp Ala Asn Leu Glu Lys Asn Tyr Cys Arg Asn Pro Asp Gly
        50                  55                  60

Asp Val Asn Gly Pro Trp Cys Tyr Thr Met Asn Pro Gln Lys Leu Phe
65                  70                  75                  80

Asp Tyr Cys Asp Val Pro Gln Cys Glu Ser Ser Pro Phe Asp Cys Gly
                85                  90                  95

Lys Pro Lys Val Glu Pro Lys Lys Cys Ser Gly Arg Ile Val Gly Gly
                100                 105                 110

Cys Val Ala Ile Ala His Ser Trp Pro Trp Gln Ile Ser Leu Arg Thr
            115                 120                 125

Arg Phe Gly Arg His Phe Cys Gly Gly Thr Leu Ile Ser Pro Glu Trp
        130                 135                 140

Val Leu Thr Ala Ala His Cys Leu Glu Arg Ser Ser Arg Pro Ser Thr
145                 150                 155                 160

Tyr Lys Val Val Leu Gly Thr His His Glu Leu Arg Leu Ala Ala Gly
                165                 170                 175

Ala Gln Gln Ile Asp Val Ser Lys Leu Phe Leu Glu Pro Ser Arg Ala
            180                 185                 190

Asp Ile Ala Leu Leu Lys Leu Ser Ser Pro Ala Ile Ile Thr Gln Asn
        195                 200                 205

Val Ile Pro Ala Cys Leu Pro Pro Ala Asp Tyr Val Val Ala Asn Trp
        210                 215                 220

Ala Glu Cys Phe Val Thr Gly Trp Gly Glu Thr Gln Asp Ser Ser Asn
225                 230                 235                 240

Ala Gly Val Leu Lys Glu Ala Gln Leu Pro Val Ile Glu Asn Lys Val
                245                 250                 255

Cys Asn Arg Tyr Glu Tyr Leu Asn Gly Arg Val Lys Ser Thr Glu Leu
            260                 265                 270

Cys Ala Gly His Leu Val Gly Gly Val Asp Ser Cys Gln Gly Asp Ser
        275                 280                 285

Gly Gly Pro Leu Val Cys Phe Glu Lys Asp Lys Tyr Ile Leu Gln Gly
        290                 295                 300

Val Thr Ser Trp Gly Leu Gly Cys Ala Arg Pro Asn Lys Pro Gly Val
305                 310                 315                 320

Tyr Val Arg Val Ser Ser Phe Ile Asn Trp Ile Glu Arg Ile Met Gln
                325                 330                 335

Ser Asn (2) INFORMATION FOR SEQ ID NO:11:

(i) SEQUENCE CHARACTERISTICS:
        (A) LENGTH: 810 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:
```

-continued

```
Met Glu His Lys Glu Val Val Leu Leu Leu Leu Phe Leu Lys Ser
 1               5                  10                  15

Gly Gln Gly Glu Pro Leu Asp Asp Tyr Val Asn Thr Lys Gly Ala Ser
                20                  25                  30

Leu Phe Ser Ile Thr Lys Lys Gln Leu Gly Ala Gly Ser Ile Glu Glu
            35                  40                  45

Cys Ala Ala Lys Cys Glu Glu Glu Glu Phe Thr Cys Arg Ser Phe
 50                  55                  60

Gln Tyr His Ser Lys Glu Gln Gln Cys Val Ile Met Ala Glu Asn Arg
 65                  70                  75                  80

Lys Ser Ser Ile Val Phe Arg Met Arg Asp Val Val Leu Phe Glu Lys
                85                  90                  95

Lys Val Tyr Leu Ser Glu Cys Lys Thr Gly Asn Gly Lys Asn Tyr Arg
                100                 105                 110

Gly Thr Met Ser Lys Thr Arg Thr Gly Ile Thr Cys Gln Lys Trp Ser
                115                 120                 125

Ser Thr Ser Pro His Arg Pro Thr Phe Ser Pro Ala Thr His Pro Ser
130                 135                 140

Glu Gly Leu Glu Glu Asn Tyr Cys Arg Asn Pro Asp Asn Asp Gly Gln
145                 150                 155                 160

Gly Pro Trp Cys Tyr Thr Thr Asp Pro Glu Arg Phe Asp Tyr Cys
                165                 170                 175

Asp Ile Pro Glu Cys Glu Asp Glu Cys Met His Cys Ser Gly Glu Asn
                180                 185                 190

Tyr Asp Gly Lys Ile Ser Lys Thr Met Ser Gly Leu Glu Cys Gln Ala
                195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
                260                 265                 270

Tyr Gln Cys Leu Lys Gly Thr Gly Glu Asn Tyr Arg Gly Asp Val Ala
                275                 280                 285

Val Thr Val Ser Gly His Thr Cys His Gly Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Glu Lys Ala Pro Trp Cys Tyr
                325                 330                 335

Thr Thr Asn Ser Gln Val Arg Trp Glu Tyr Cys Lys Ile Pro Ser Cys
                340                 345                 350

Glu Ser Ser Pro Val Ser Thr Glu Pro Leu Asp Pro Thr Ala Pro Pro
                355                 360                 365

Glu Leu Thr Pro Val Val Gln Glu Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Trp His Glu Lys Thr Pro Glu Asn Phe
                405                 410                 415

Pro Asn Ala Gly Leu Thr Met Asn Tyr Cys Arg Asn Pro Asp Ala Asp
```

-continued

```
                420                 425                 430
Lys Gly Pro Trp Cys Phe Thr Thr Asp Pro Ser Val Arg Trp Glu Tyr
            435                 440                 445
Cys Asn Leu Lys Lys Cys Ser Gly Thr Glu Gly Ser Val Ala Ala Pro
            450                 455                 460
Pro Pro Val Ala Gln Leu Pro Asp Ala Glu Thr Pro Ser Glu Glu Asp
465                 470                 475                 480
Cys Met Phe Gly Asn Gly Lys Gly Tyr Arg Gly Lys Lys Ala Thr Thr
                485                 490                 495
Val Thr Gly Thr Pro Cys Gln Glu Trp Ala Ala Gln Glu Pro His Ser
                500                 505                 510
His Arg Ile Phe Thr Pro Glu Thr Asn Pro Arg Ala Gly Leu Glu Lys
            515                 520                 525
Asn Tyr Cys Arg Asn Pro Asp Gly Asp Val Gly Gly Pro Trp Cys Tyr
            530                 535                 540
Thr Thr Asn Pro Arg Lys Leu Phe Asp Tyr Cys Asp Val Pro Gln Cys
545                 550                 555                 560
Ala Ala Ser Ser Phe Asp Cys Gly Lys Pro Gln Val Glu Pro Lys Lys
                565                 570                 575
Cys Pro Gly Arg Val Val Gly Gly Cys Val Ala Tyr Pro His Ser Trp
                580                 585                 590
Pro Trp Gln Ile Ser Leu Arg Thr Arg Leu Gly Met His Phe Cys Gly
            595                 600                 605
Gly Thr Leu Ile Ser Pro Glu Trp Val Leu Thr Ala Ala His Cys Leu
            610                 615                 620
Glu Lys Ser Ser Arg Pro Ser Phe Tyr Lys Val Ile Leu Gly Ala His
625                 630                 635                 640
Arg Glu Val His Leu Glu Pro His Val Gln Glu Ile Glu Val Ser Lys
                645                 650                 655
Met Phe Ser Glu Pro Ala Arg Ala Asp Ile Ala Leu Leu Lys Leu Ser
                660                 665                 670
Ser Pro Ala Ile Ile Thr Asp Lys Val Ile Pro Ala Cys Leu Pro Ser
            675                 680                 685
Pro Asn Tyr Val Val Ala Asp Arg Thr Glu Cys Phe Ile Thr Gly Trp
            690                 695                 700
Gly Glu Thr Gln Gly Thr Tyr Gly Ala Gly Leu Leu Lys Glu Ala Arg
705                 710                 715                 720
Leu Pro Val Ile Glu Asn Lys Val Cys Asn Arg Tyr Glu Phe Leu Asn
                725                 730                 735
Gly Thr Val Lys Thr Thr Glu Leu Cys Ala Gly His Leu Ala Gly Gly
                740                 745                 750
Thr Asp Ser Cys Gln Gly Asp Ser Gly Gly Pro Leu Val Cys Phe Glu
            755                 760                 765
Lys Asp Lys Tyr Ile Leu Gln Gly Val Thr Ser Trp Gly Leu Gly Cys
            770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810
```

(2) INFORMATION FOR SEQ ID NO:12:

(i) SEQUENCE CHARACTERISTICS:
        (A) LENGTH: 812 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met Asp His Lys Glu Val Ile Leu Leu Phe Leu Leu Leu Leu Lys Pro
1               5                   10                  15

Gly Gln Gly Asp Ser Leu Asp Gly Tyr Ile Ser Thr Gln Gly Ala Ser
            20                  25                  30

Leu Phe Ser Leu Thr Lys Lys Gln Leu Ala Ala Gly Gly Val Ser Asp
        35                  40                  45

Cys Leu Ala Lys Cys Glu Gly Glu Thr Asp Phe Val Cys Arg Ser Phe
    50                  55                  60

Gln Tyr His Ser Lys Glu Gln Gln Cys Val Ile Met Ala Glu Asn Ser
65                  70                  75                  80

Lys Thr Ser Ser Ile Ile Arg Met Arg Asp Val Ile Leu Phe Glu Lys
                85                  90                  95

Arg Val Tyr Leu Ser Glu Cys Lys Thr Gly Ile Gly Asn Gly Tyr Arg
            100                 105                 110

Gly Thr Met Ser Arg Thr Lys Ser Gly Val Ala Cys Gln Lys Trp Gly
        115                 120                 125

Ala Thr Phe Pro His Val Pro Asn Tyr Ser Pro Ser Thr His Pro Asn
    130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asp Pro Asp Lys Arg Tyr Asp Tyr Cys
            165                 170                 175

Asn Ile Pro Glu Cys Glu Glu Cys Met Tyr Cys Ser Gly Glu Lys
            180                 185                 190

Tyr Glu Gly Lys Ile Ser Lys Thr Met Ser Gly Leu Asp Cys Gln Ala
            195                 200                 205

Trp Asp Ser Gln Ser Pro His Ala His Gly Tyr Ile Pro Ala Lys Phe
    210                 215                 220

Pro Ser Lys Asn Leu Lys Met Asn Tyr Cys His Asn Pro Asp Gly Glu
225                 230                 235                 240

Pro Arg Pro Trp Cys Phe Thr Thr Asp Pro Thr Lys Arg Trp Glu Tyr
            245                 250                 255

Cys Asp Ile Pro Arg Cys Thr Thr Pro Pro Pro Pro Ser Pro Thr
            260                 265                 270

Tyr Gln Cys Leu Lys Gly Arg Gly Glu Asn Tyr Arg Gly Thr Val Ser
    275                 280                 285

Val Thr Val Ser Gly Lys Thr Cys Gln Arg Trp Ser Glu Gln Thr Pro
290                 295                 300

His Arg His Asn Arg Thr Pro Glu Asn Phe Pro Cys Lys Asn Leu Glu
305                 310                 315                 320

Glu Asn Tyr Cys Arg Asn Pro Asp Gly Glu Thr Ala Pro Trp Cys Tyr
            325                 330                 335

Thr Thr Asp Ser Gln Leu Arg Trp Glu Tyr Cys Glu Ile Pro Ser Cys
        340                 345                 350

Glu Ser Ser Ala Ser Pro Asp Gln Ser Asp Ser Ser Val Pro Pro Glu
    355                 360                 365

Glu Gln Thr Pro Val Val Gln Glu Cys Tyr Gln Ser Asp Gly Gln Ser
370                 375                 380

-continued

```
Tyr Arg Gly Thr Ser Ser Thr Ile Thr Gly Lys Lys Cys Gln Ser
385                 390                 395                 400

Trp Ala Ala Met Phe Pro His Arg His Ser Lys Thr Pro Glu Asn Phe
            405                 410                 415

Pro Asp Ala Gly Leu Glu Met Asn Tyr Cys Arg Asn Pro Asp Gly Asp
                420                 425                 430

Lys Gly Pro Trp Cys Tyr Thr Thr Asp Pro Ser Val Arg Trp Glu Tyr
            435                 440                 445

Cys Asn Leu Lys Arg Cys Ser Glu Thr Gly Ser Val Val Glu Leu
450                 455                 460

Pro Thr Val Ser Gln Glu Pro Ser Gly Pro Ser Asp Ser Glu Thr Asp
465                 470                 475                 480

Cys Met Tyr Gly Asn Gly Lys Asp Tyr Arg Gly Lys Thr Ala Val Thr
                485                 490                 495

Ala Ala Gly Thr Pro Cys Gln Gly Trp Ala Ala Gln Glu Pro His Arg
            500                 505                 510

His Ser Ile Phe Thr Pro Gln Thr Asn Pro Arg Ala Asp Leu Glu Lys
            515                 520                 525

Asn Tyr Cys Arg Asn Pro Asp Gly Asp Val Asn Gly Pro Trp Cys Tyr
530                 535                 540

Thr Thr Asn Pro Arg Lys Leu Tyr Asp Tyr Cys Asp Ile Pro Leu Cys
545                 550                 555                 560

Ala Ser Ala Ser Ser Phe Glu Cys Gly Lys Pro Gln Val Glu Pro Lys
                565                 570                 575

Lys Cys Pro Gly Arg Val Val Gly Gly Cys Val Ala Asn Pro His Ser
            580                 585                 590

Trp Pro Trp Gln Ile Ser Leu Arg Thr Arg Phe Thr Gly Gln His Phe
            595                 600                 605

Cys Gly Gly Thr Leu Ile Ala Pro Glu Trp Val Leu Thr Ala Ala His
610                 615                 620

Cys Leu Glu Lys Ser Ser Arg Pro Glu Phe Tyr Lys Val Ile Leu Gly
625                 630                 635                 640

Ala His Glu Glu Tyr Ile Arg Gly Leu Asp Val Gln Glu Ile Ser Val
                645                 650                 655

Ala Lys Leu Ile Leu Glu Pro Asn Asn Arg Asp Ile Ala Leu Leu Lys
            660                 665                 670

Leu Ser Arg Pro Ala Thr Ile Thr Asp Lys Val Ile Pro Ala Cys Leu
            675                 680                 685

Pro Ser Pro Asn Tyr Met Val Ala Asp Arg Thr Ile Cys Tyr Ile Thr
690                 695                 700

Gly Trp Gly Glu Thr Gln Gly Thr Phe Gly Ala Gly Arg Leu Lys Glu
705                 710                 715                 720

Ala Gln Leu Pro Val Ile Glu Asn Lys Val Cys Asn Arg Val Glu Tyr
                725                 730                 735

Leu Asn Asn Arg Val Lys Ser Thr Glu Leu Cys Ala Gly Gln Leu Ala
            740                 745                 750

Gly Gly Val Asp Ser Cys Gln Gly Asp Ser Gly Gly Pro Leu Val Cys
            755                 760                 765

Phe Glu Lys Asp Lys Tyr Ile Leu Gln Gly Val Thr Ser Trp Gly Leu
770                 775                 780

Gly Cys Ala Arg Pro Asn Lys Pro Gly Val Tyr Val Arg Val Ser Arg
785                 790                 795                 800
```

```
Phe Val Asp Trp Ile Glu Arg Glu Met Arg Asn Asn
            805                 810
```

(2) INFORMATION FOR SEQ ID NO:13:

(i) SEQUENCE CHARACTERISTICS:
        (A) LENGTH: 790 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Asp Ser Leu Asp Asp Tyr Val Asn Thr Gln Gly Ala Phe Leu Phe Ser
1               5                   10                  15

Leu Ser Arg Lys Gln Val Ala Ala Arg Ser Val Glu Glu Cys Ala Ala
            20                  25                  30

Lys Cys Glu Ala Glu Thr Asn Phe Ile Cys Arg Ala Phe Gln Tyr His
            35                  40                  45

Ser Lys Asp Gln Gln Cys Val Val Met Ala Glu Asn Ser Lys Thr Ser
50                  55                  60

Pro Ile Ala Arg Met Arg Asp Val Val Leu Phe Glu Lys Arg Ile Tyr
65                  70                  75                  80

Leu Ser Glu Cys Lys Thr Gly Asn Gly Lys Asn Tyr Arg Gly Thr Thr
            85                  90                  95

Ser Lys Thr Lys Ser Gly Val Ile Cys Gln Lys Trp Ser Val Ser Ser
            100                 105                 110

Pro His Ile Pro Lys Tyr Ser Pro Glu Lys Phe Pro Leu Ala Gly Leu
            115                 120                 125

Glu Glu Asn Tyr Cys Arg Asn Pro Asp Asn Asp Glu Lys Gly Pro Trp
130                 135                 140

Cys Tyr Thr Thr Asp Pro Glu Thr Arg Phe Asp Tyr Cys Asp Ile Pro
145                 150                 155                 160

Glu Cys Glu Asp Glu Cys Met His Cys Ser Gly Glu His Tyr Glu Gly
            165                 170                 175

Lys Ile Ser Lys Thr Met Ser Gly Ile Glu Cys Gln Ser Trp Gly Ser
            180                 185                 190

Gln Ser Pro His Ala His Gly Tyr Leu Pro Ser Lys Phe Pro Asn Lys
            195                 200                 205

Asn Leu Lys Met Asn Tyr Cys Arg Asn Pro Asp Gly Glu Pro Arg Pro
210                 215                 220

Trp Cys Phe Thr Thr Asp Pro Asn Lys Arg Trp Glu Phe Cys Asp Ile
225                 230                 235                 240

Pro Arg Cys Thr Thr Pro Pro Thr Ser Gly Pro Thr Tyr Gln Cys
            245                 250                 255

Leu Lys Gly Arg Gly Glu Asn Tyr Arg Gly Thr Val Ser Val Thr Ala
            260                 265                 270

Ser Gly His Thr Cys Gln Arg Trp Ser Ala Gln Ser Pro His Lys His
            275                 280                 285

Asn Arg Thr Pro Glu Asn Phe Pro Cys Lys Asn Leu Glu Glu Asn Tyr
            290                 295                 300

Cys Arg Asn Pro Asp Gly Glu Thr Ala Pro Trp Cys Tyr Thr Thr Asp
305                 310                 315                 320

Ser Glu Val Arg Trp Asp Tyr Cys Lys Ile Pro Ser Cys Gly Ser Ser
            325                 330                 335
```

-continued

```
Thr Thr Ser Thr Glu His Leu Asp Ala Pro Val Pro Glu Gln Thr
            340                 345                 350

Pro Val Ala Gln Asp Cys Tyr Arg Gly Asn Gly Glu Ser Tyr Arg Gly
            355                 360                 365

Thr Ser Ser Thr Thr Ile Thr Gly Arg Lys Cys Gln Ser Trp Val Ser
            370                 375                 380

Met Thr Pro His Arg His Glu Lys Thr Pro Gly Asn Phe Pro Asn Ala
385                 390                 395                 400

Gly Leu Thr Met Asn Tyr Cys Arg Asn Pro Asp Ala Asp Lys Ser Pro
                405                 410                 415

Trp Cys Tyr Thr Thr Asp Pro Arg Val Arg Trp Glu Tyr Cys Asn Leu
                420                 425                 430

Lys Lys Cys Ser Glu Thr Glu Gln Gln Val Thr Asn Phe Pro Ala Ile
            435                 440                 445

Ala Gln Val Pro Ser Val Glu Asp Leu Ser Glu Asp Cys Met Phe Gly
            450                 455                 460

Asn Gly Lys Arg Tyr Arg Gly Lys Arg Ala Thr Thr Val Ala Gly Val
465                 470                 475                 480

Pro Cys Gln Glu Trp Ala Ala Gln Glu Pro His Arg His Ser Ile Phe
                485                 490                 495

Thr Pro Glu Thr Asn Pro Arg Ala Gly Leu Glu Lys Asn Tyr Cys Arg
            500                 505                 510

Asn Pro Asp Gly Asp Asp Asn Gly Pro Trp Cys Tyr Thr Thr Asn Pro
            515                 520                 525

Gln Lys Leu Phe Asp Tyr Cys Asp Val Pro Gln Cys Val Thr Ser Ser
            530                 535                 540

Phe Asp Cys Gly Lys Pro Lys Val Glu Pro Lys Lys Cys Pro Ala Arg
545                 550                 555                 560

Val Val Gly Gly Cys Val Ser Ile Pro His Ser Trp Pro Trp Gln Ile
                565                 570                 575

Ser Leu Arg Tyr Arg Tyr Arg Gly His Phe Cys Gly Gly Thr Leu Ile
            580                 585                 590

Ser Pro Glu Trp Val Leu Thr Ala Lys His Cys Leu Glu Lys Ser Ser
            595                 600                 605

Ser Pro Ser Ser Tyr Lys Val Ile Leu Gly Ala His Glu Glu Tyr His
            610                 615                 620

Leu Gly Glu Gly Val Gln Glu Ile Asp Val Ser Lys Leu Phe Lys Glu
625                 630                 635                 640

Pro Ser Glu Ala Asp Ile Ala Leu Leu Lys Leu Ser Pro Ala Val
                645                 650                 655

Ile Thr Asp Lys Val Ile Pro Ala Cys Leu Pro Thr Pro Asn Tyr Val
                660                 665                 670

Val Ala Asp Arg Thr Ala Cys Tyr Ile Thr Gly Trp Gly Glu Thr Lys
            675                 680                 685

Gly Thr Tyr Gly Ala Gly Leu Leu Lys Glu Ala Arg Leu Pro Val Ile
        690                 695                 700

Glu Asn Lys Val Cys Asn Arg Tyr Glu Tyr Leu Gly Gly Lys Val Ser
705                 710                 715                 720

Pro Asn Glu Leu Cys Ala Gly His Leu Ala Gly Ile Asp Ser Cys
                725                 730                 735

Gln Gly Asp Ser Gly Gly Pro Leu Val Cys Phe Glu Lys Asp Lys Tyr
            740                 745                 750

Ile Leu Gln Gly Val Thr Ser Trp Gly Leu Gly Cys Ala Leu Pro Asn
```

```
                    755                 760                 765
Lys Pro Gly Val Tyr Val Arg Val Ser Arg Phe Val Thr Trp Ile Glu
    770                 775                 780
Glu Ile Met Arg Arg Asn
785                 790
```

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (xi) SEQUENCE DESCRIPTION: SEQ ID NO:14:

HAWAAUGUCU                                                            10

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ala Ala Pro Val
1

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ala Ala Pro Ala
1

METHODS AND COMPOSITIONS FOR GENERATING ANGIOSTATIN

This application is a continuation-in-part of application Ser. No. 08/710,305, filed Sep. 17, 1996 now patented U.S. Pat. No. 5,808,012. Benefit of PCT application PCT/US97/16539 filed Sep. 17, 1997 is also claimed as a continuation.

FIELD OF THE INVENTION

This invention relates to angiostatin, an inhibitor of angiogenesis.

BACKGROUND OF THE INVENTION

Angiostatin, a proteolytic fragment of plasminogen believed to consist of kringles 1 through 3 and all or part of kringle 4 is a potent inhibitor of angiogenesis and the growth of tumor cell metastases. O'Reilly et al., *Cell*, 79, 315–328 (1994); PCT application WO 95/29242. Angiostatin is found in vivo in tumor-bearing mice. O'Reilly et al., *Cell*, 79, 315–328 (1994); O'Reilly et al., *Nature Med.* 2, 689–692 (1996). The enzymatic mechanism by which angiostatin is generated in vivo remains unknown.

Angiostatin activity can be generated in vitro by limited elastase proteolysis of plasminogen. Sottrup-Jensen et al. in *Progress in Chemical Fibrinolysis and Thrombolysis*, 3, 191–209 (Davidson et al. eds. 1978). A recent abstract proposes that angiostatin is generated by macrophages infiltrating primary tumors and releasing elastase activity, which then cleaves plasminogen to form a protein having angiostatin activity. Dong et al., *Proc. Am. Assoc. Cancer Res.*, 37 58 (1996). However, while limited elastase cleavage of plasminogen will yield a fragment or fragments having angiostatin activity, elastase will further digest the fragment(s) to inactive peptides, and therefore, is probably not the enzyme that generates angiostatin in vivo.

As noted above, angiostatin may be generated in vitro by limited elastase proteolysis of plasminogen. This method has several disadvantages. First, while elastase cleaves plasminogen to generate a fragment containing kringles 1–3, it is not known if this cleavage is at the normal sites where cleavage occurs to produce angiostatin in vivo. Therefore, the elastase-derived angiostatin may have altered in vivo processing with altered activity in humans. It may also be immunogenic if the sites of peptide cleavage are different from normal angiostatin.

A second means of producing angiostatin is by expressing the desired kringle domains of the plasminogen cDNA or gene in an expression vector in prokaryotic or eukaryotic cells. See PCT application WO 95/29242. This approach is also limited since the appropriate domains to express are not known. The product may also be immunogenic and may not be processed in humans as would be the product generated by cleavage of plasminogen by the normal in vivo enzymes.

Finally, angiostatin can be isolated from the body fluids of animals in which it is produced. See PCT application WO 95/29242. However, angiostatin cannot be produced in sufficient quantities for disease treatment in this manner, and the angiostatin may be contaminated with infectious agents when isolated from such sources.

Clearly a need exists for a method of producing native angiostatin in large quantities. "Native angiostatin" is defined herein to be the angiostatin produced in vivo or angiostatin, no matter how produced, which is the same as the angiostatin produced in vivo.

SUMMARY OF THE INVENTION

The present invention provides such methods. These methods are based on the discovery that a conditioned culture medium (CCM) produced by culturing cancer cells, primary endothelial cells, smooth muscle cells or fibroblasts produces angiostatin when contacted with plasminogen or plasmin. The active factors in the CCM have been identified to be a plasminogen activator and a sulfhydryl donor. Thus, the angiostatin produced by the use of a plasminogen activator and sulfhydryl donor is the same as angiostatin produced in vivo, i.e., it is native angiostatin.

In one method of the invention for producing angiostatin in vitro, plasmin is contacted with a sulfhydryl donor to produce the angiostatin. The plasmin may be generated by contacting plasminogen with a plasminogen activator. Most conveniently, all of the reactants (plasminogen, plasminogen activator and sulfhydryl donor) can be contacted simultaneously to produce the angiostatin.

The angiostatin produced by this method, along with any remaining reactants, or angiostatin purified or partially purified from the reactants, may be administered to an animal, including a human, in need thereof. Animals in need of angiostatin are animals suffering from an angiogenic disease.

The invention further provides a composition for generating angiostatin. The composition comprises a sulfhydryl donor and a plasminogen activator. Two embodiments of the composition are CCM produced by culturing cells capable of producing plasminogen activator and a lysate of such cells.

The invention also provides a method of treating an angiogenic disease comprising administering to an animal suffering from such a disease an amount of a sulfhydryl donor effective to cause the conversion of plasmin to angiostatin. The plasmin may be that produced by endogenous plasminogen activator(s) from endogenous plasminogen. Alternatively, the method may further comprise administering an effective amount of plasmin. In yet other embodiments, a plasminogen activator may be administered to the animal to produce the plasmin from endogenous plasminogen or from an effective amount of administered plasminogen.

The invention further provides a container holding a plasminogen activator, alone or in combination with sulfhydryl donor. The container has a label thereon instructing administration of the plasminogen activator or the combination of the plasminogen activator and sulfhydryl donor to an animal suffering from an angiogenic disease. The invention also provides a container holding a sulfhydryl donor with a label thereon instructing administration of the sulfhydryl donor in an amount effective to cause the conversion of plasmin to angiostatin.

The invention also provides a protein having the following characteristics: (a) it is a fragment of plasminogen; (b) its N-terminal amino acid is the same as the N-terminal amino acid of plasmin; (c) its C-terminal amino acid is in kringle 5; and (d) it inhibits angiogenesis. In one embodiment, the protein is native angiostatin. The invention further provides a DNA molecule coding for the protein, the DNA molecule operatively linked to expression control sequences, a host cell comprising the DNA molecule operatively linked to expression control sequences, and a method of producing the protein comprising culturing the host cell. The protein may be used to treat angiogenic diseases by administering an effective amount of the protein to an animal suffering from such a disease. An animal suffering from such a disease may also be treated by administering to it a transgene coding for the protein. Preferably, the protein coded for by the transgene is native angiostatin.

Finally, the invention provides an antibody which binds selectively to the protein. Such an antibody may be used to purify the protein from materials containing it. Also, such an antibody which binds selectively to native angiostatin may be used in methods and kits to detect or quantitate native angiostatin.

BRIEF DESCRIPTION OF THE DRAWINGS

FIG. 3A: Endothelial cell proliferation. The data are mean±standard deviation. FIG. 3B: Basic fibroblast growth factor (bFGF)-induced migration. Background migration without the inducer and in the presence of stimulatory bFGF are indicated. Toxicity was measured in parallel by trypan blue exclusion and was <10% at all concentrations.

FIG. 4A: Control HUVEC form branching, interconnecting networks. FIG. 4B: By contrast angiostatin produced using PC-3 SFCM caused a significant disruption of the tube network.

FIGS. 5A–B: Photographs showing the inhibition of angiogenesis in vivo by angiostatin produced using PC-3 SCFM. FIG. 5A: A hydron pellet (indicated by the arrow) containing bFGF induced a positive neovascular response 7 days after implantation. FIG. 5B: By contrast, no vessels are observed approaching a hydron pellet containing bFGF and 10 μg/ml angiostatin produced using PC-3 SFCM (indicated by the arrow).

FIG. 7: Graph showing that urokinase-type plasminogen activator (u-PA) activity and plasminogen-angiostatin converting activity (PACA) co-elute on a gradient elution from Hi-Q anion exchange column. Optical density readings at 280 nm demonstrated several protein peaks. u-PA activity was determined by measuring the cleavage of a chromogenic peptide substrate for plasmin (Val-Leu-Lys p-NA) at 405 nm. The peak fractions were assayed for PACA by western blot.

PLG=human plasminogen;
uPA=urokinase-type plasminogen activator;

tPA=tissue-type plasminogen activator;

SK=streptokinase;

+=with N-acetyl-L-cysteine; and

−=without N-acetyl-L-cysteine.

Figures 12, 13:
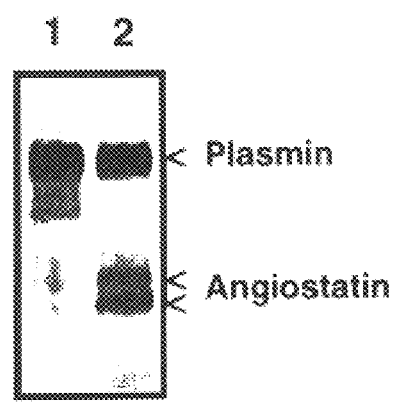
FIG. 12: Western blot showing the production of angiostatin by u-PA, t-PA and streptokinase. The abbreviations used in the figure have the following meanings.

FIG. 13: Western blot showing the production of plasmin from plasminogen and the production of angiostatin from the pre-formed, purified plasmin. Lane 1—plasminogen+u-PA-Sepharose; Lane 2—purified plasmin+100 μM N-acetyl-L-cysteine.

Figure 14:
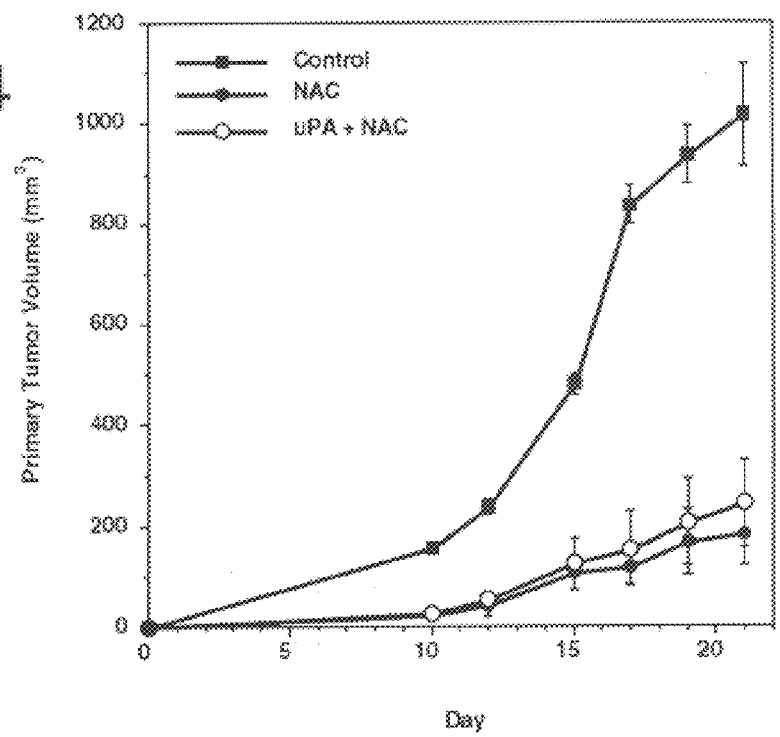

FIG. 14: Graph of mean primary tumor size (mm$^3$) for days 0–21 for control mice and mice treated with N-acetyl-L-cysteine (NAC) or NAC+urokinase-type plasminogen inhibitor (uPA).

Figure 15:
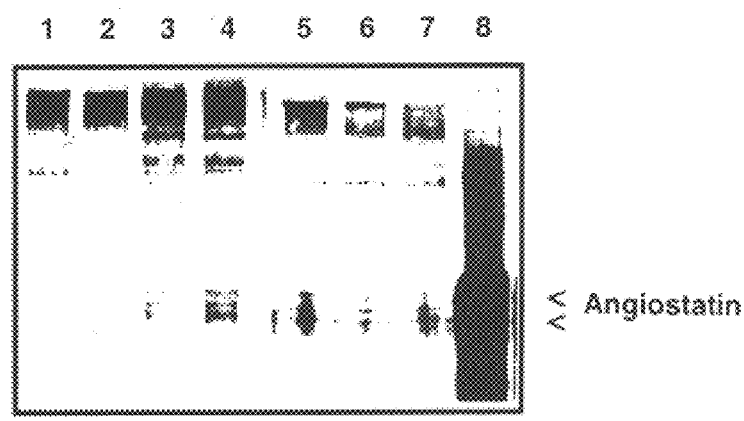

FIG. 15: Western blot showing the production of angiostatin by N-acetyl-L-cysteine (NAC) in vivo. Lane 1—plasma (diluted 1:20) from control mouse #2; Lane 2—plasma (diluted 1:20) from control mouse #3; Lane 3—plasma (diluted 1:20) from first mouse receiving affinity-purified, cell-free angiostatin; Lane 4—plasma (diluted 1:20) from second mouse receiving affinity-purified, cell-free angiostatin; Lane 5—plasma (diluted 1:20) from NAC-treated mouse #1; Lane 6 plasma (diluted 1:20) from NAC-treated mouse #2; Lane 7—plasma (diluted 1:20) from NAC-treated mouse #3; and Lane 8—affinity-purified, cell-free angiostatin.

Figure 16:
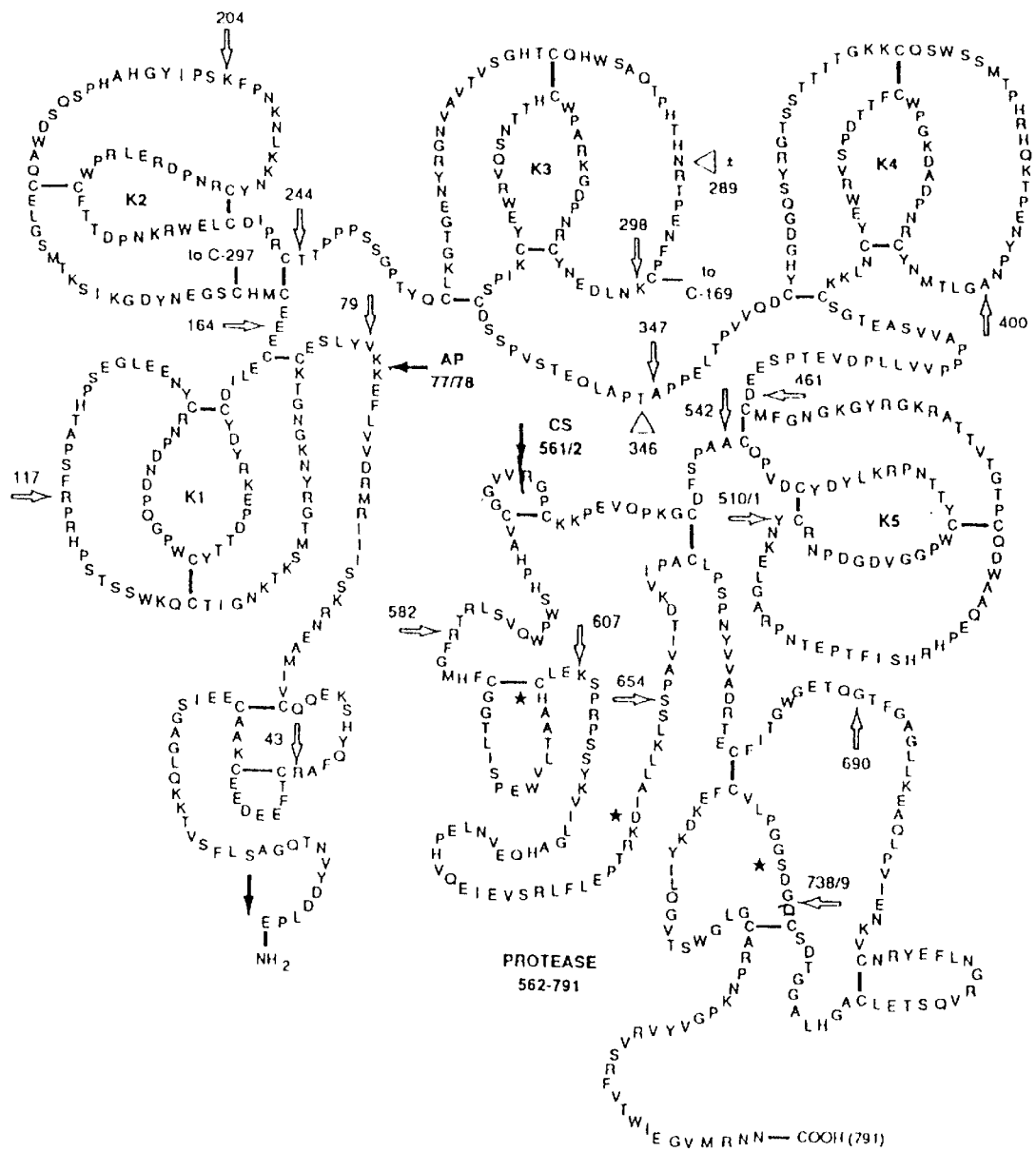

FIG. 16: A diagram of human plasminogen showing the amino acid sequence of the complete molecule after cleavage of the signal peptide (not shown) (taken from *Molecular Basis of Thrombosis and Hemostasis* (High and Roberts, eds. 1995)). Kringles 1–5 (K1–K5) are indicated. The cleavage sites between residues 77 and 78 and residues 561 and 562 needed for activation of plasminogen to plasmin are indicated by filled arrows. The unfilled arrows represent the positions of introns in the gene. The locations of the N-linked oligosaccharide at position 289 and the O-linked glycan at position 346 are also indicated. The * indicate members of the catalytic triad of plasmin (His603, Asp646 and Ser741).

DETAILED DESCRIPTION OF THE PRESENTLY PREFERRED EMBODIMENTS

The invention provides in vitro methods of generating native angiostatin. One such method comprises contacting plasminogen with a plasminogen activator and a sulfhydryl donor. All three of the reactants may be combined simultaneously. Alternatively, the plasminogen may be contacted with a plasminogen activator to produce plasmin, and the plasmin then contacted with a sulfhydryl donor to produce the angiostatin. The plasmin may be at least partially purified prior to contacting it with the sulfhydryl donor. Indeed, angiostatin can be produced directly from plasmin, however made, by contacting the plasmin with a sulfhydryl donor.

The plasminogen may be from any animal species. Preferably, however, plasminogen from the species of animal to be treated with the angiostatin is used to avoid immune reactions upon administration of the angiostatin. Thus, if a human is to be treated with the angiostatin, human plasminogen is preferably used.

Methods of making plasminogen are well known in the art. Plasminogen may also be purchased commercially. Preferably the plasminogen is prepared by recombinant DNA or other techniques that avoid the inclusion of infectious agents in the plasminogen preparation.

All types of plasminogen activators may be used, including urokinase-type plasminogen activators, tissue-type plasminogen activators and streptokinase. The plasminogen activator may be from any animal species. Methods of making plasminogen activators are well known in the art, and many plasminogen activators are available commercially. Preferably the plasminogen activator is prepared by recombinant DNA or other techniques that avoid the inclusion of infectious agents in the plasminogen activator preparation.

The plasminogen is contacted with the plasminogen activator in amounts and under conditions effective to cause the conversion of the plasminogen to plasmin. These amounts and conditions are known or can be determined empirically as is known in the art. In particular, from about 1 ng/ml to about 1 μg/ml of urokinase plasminogen activator for each microgram of plasminogen in a 1 ml reaction have been found to give complete conversion of plasminogen to plasmin after about 24 hours of incubation at 37° C.

Any sulfhydryl donor may be used. Sulfhydryl donors are well known and are available commercially. Suitable sulfhydryl donors include L-cysteine, D-cysteine, DL-cysteine, N-acetyl-L-cysteine, reduced glutathione, D-penicillamine and captopril. The sulfhydryl donor is believed to reduce or alter disulfide bond formation in the plasminogen, and/or the plasmin, and/or the angiostatin, and/or an intermediate product.

The sulfhydryl donor is contacted with the plasmin, alone or in the presence of the plasminogen and plasminogen activator, in amounts and under conditions effective to cause the conversion of the plasmin to angiostatin. These amounts and conditions can be determined empirically as is known in the art. In particular, from about 10 μM to about 1 mM of sulfhydryl donor for each microgram of plasmin in a 1 ml reaction have been found to give complete conversion of plasmin to angiostatin after about 24 hours of incubation at 37° C.

Plasmin may be generated from plasminogen by a plasminogen activator as described above. The plasmin may be purified from the reactants prior to contacting it with the sulfhydryl donor. Methods of purifying plasmin are known in the art (see, e.g., Example 4). Plasmin purchased commercially or prepared in other ways may also be used to produce angiostatin by contacting the plasmin with a sulfyhydryl donor as described above.

The invention further provides a composition for generating angiostatin. The composition comprises a plasminogen activator and a sulfhydryl donor as described above. The plasminogen activator and sulfhydryl donor may be contained in any physiologically-acceptable solution (e.g., saline, buffers, culture medium) or may be present in crystalline or lyophilized form. Compositions suitable for therapeutic use are described below.

The composition may be a conditioned culture medium (CCM) prepared by culturing cells capable of producing plasminogen activator. Malignant animal cells, human and non-human, which express a plasminogen activator can produce CCM capable of converting plasminogen and plasmin into angiostatin. Suitable malignant cells include human prostate carcinoma cell lines PC-3, DU-145, LN-CaP, human breast carcinoma cell lines MDA-MB-231 and MCF-7, human glioma cell lines U-373, U-118, A-172, and U-87, and mouse melanoma cell line B16F10. Many non-malignant animal cells are known to produce plasminogen activator. Suitable non-malignant cells include primary endothelial cells (e.g., bovine aortic endothelial cells), smooth muscle cells (e.g., bovine smooth muscle cells), and fibroblasts. In addition, bacterial cells are known which produce plasminogen activator (e.g., streptokinase), and cells of any type can be transformed by recombinant DNA techniques to produce plasminogen activator. Suitable cells and cell lines are well known in the art and may be obtained commercially, from cell depositories, and by methods well known in the art.

Suitable culture conditions for these cells are also well known in the art. The culture medium used must contain a sulfhydryl donor, or a sulfhydryl donor may be added to the CCM after it is produced. Suitable culture media include those available commercially, such as RPMI, DMEM, etc. The CCM may be produced by simply culturing the cells under normal culture conditions for a sufficient time to produce CCM capable of converting plasminogen or plasmin to angiostatin. This time can be determined empirically. In particular, it has been found that culturing the mammalian cells for 24–72 hours after a monolayer has formed at 37° C. is sufficient.

Alternatively, or in addition, the cells can be lysed after culturing for a time sufficient to allow synthesis of plasminogen activator. This time can be determined empirically, but culturing the cells until a monolayer has formed should be sufficient. The lysate can be used to convert plasminogen and plasmin to angiostatin.

The angiostatin produced by these methods may be purified from the reaction mixture. Methods of protein purification are well known in the art. In particular, angiostatin may be purified by affinity chromatography using lysine-Sepharose. Residual plasmin activity should be removed with, e.g., soybean trypsin inhibitor-Sepharose, aprotinin-Sepharose, or other affinity chromatography procedures that remove serine proteases or the plasmin catalytic domain. The angiostatin may also be purified from the reaction mixture using an antibody that binds selectively to it (see below).

The angiostatin produced by these methods (native angiostatin) has been characterized. It reacts with a monoclonal antibody specific for kringles 1–3 of plasminogen and has been found to inhibit angiogenesis as assessed by a variety of tests in vitro and in vivo.

It has also been found to have the N-terminal sequence of plasmin. For angiostatin produced from human plasminogen, the N-terminal sequence has been found to be Lys Val Tyr Leu Ser Glu Cys Lys Thr Gly [SEQ ID NO:1]. The sequences of the plasmin of other animals are known. Thus, native angiostatin of a particular animal would have the same N-terminal sequence as the plasmin of that animal.

Quite surprisingly, native angiostatin has been found to have its C-terminal amino acid located in kringle 5. In particular, angiostatin produced from human plasminogen has been found to have the C-terminal sequence Cys Tyr Thr Thr Asn Pro Arg [SEQ ID NO:4] or Cys Tyr Thr Thr Asn Pro Arg Lys [SEQ ID NO:5] (see Example 6). These C-terminal sequences would result from a cleavage after amino acid 529 or 530 of plasminogen (see FIG. 16), which are known plasmin cleavage sites. Thus, native human angiostatin comprises most of kringle 5 (see FIG. 16), which is consistent with its molecular weight of 50–60 kD on polyacrylamide gel electrophoresis under non-reducing conditions.

These findings were surprising because it had been thought that angiostatin contained kringles 1–3 and part or all of kringle 4 (see Background section). Also, it has been shown that a molecule consisting of kringles 1–4, while active, was less active than a molecule consisting of kringles 1–3 (see PCT application WO 96/35774). Thus, it was unanticipated that native angiostatin would include any portion of kringle 5. It was particularly unanticipated that native angiostatin would include most of kringle 5.

It is now expected that plasminogen fragments, other than native angiostatin, including at least a portion of kringle 5 will possess angiostatin activity (i.e., will inhibit angiogenesis). Preferably the plasminogen fragment comprises the majority of kringle 5. More preferably the plasminogen fragment comprises most of kringle 5. As used herein "majority of kringle 5" means at least 50% of kringle 5 (e.g., at least 40 amino acids for human kringle 5), and "most of kringle 5" means at least 75% of kringle 5 (e.g., at least 60 amino acids for human kringle 5). Of course, the plasminogen fragment is most preferably native angiostatin for the reasons given above.

The sequences of plasminogens from other animals are known (available from, e.g., GenBank). The sequences of human [SEQ ID NO:6], bovine [SEQ ID NO:7], canine [SEQ ID NO:8], western European hedgehog [SEQ ID NO:9], horse [SEQ ID NO:10], rhesus monkey [SEQ ID NO:11], mouse [SEQ ID NO:12], and pig [SEQ ID NO:13] plasminogen are given below in the Sequence Listing (downloaded from SWISS-PROT Protein Sequence Database). Native angiostatin for a particular animal would include most of kringle S of that animal's plasminogen and would have a C-terminal sequence corresponding to the C-terminal sequences of human native angiostatin given above. Indeed, a review of these sequences showed that the sequence immediately after the cleavage sites in human plasminogen that produce native angiostatin (SEQ ID NO:2 and SEQ ID NO:3; see Example 6 below) is conserved in all of these plasminogen sequences (see the amino acids highlighted in bold in the Sequence Listing).

As can be observed from the Sequence Listing, the sequences of canine [SEQ ID NO:8] and horse [SEQ ID NO:10] plasminogens contain only a single kringle domain. This single kringle domain is considered a kringle 5 domain by homology to other kringle 5 domains, and it contains the conserved sequence (see highlighted amino acids in the Sequence Listing) found in the kringle 5 domains of the other plasminogens. Thus, the invention includes plasminogen fragments of canine and horse plasminogens and of any other plasminogen containing a kringle 5 domain.

Plasminogen fragments of the invention (those having the N-terminal sequence of plasmin and having their C-terminal amino acids located in kringle 5) can be produced by recombinant DNA methods. Preferably the plasminogen fragment is native angiostatin. Most preferably the plasminogen fragment is native human angiostatin. Recombinant DNA methods and suitable host cells, vectors and other reagents for use therein, are well known in the art.

The selection of a particular host cell for production of a plasminogen fragment of the invention is dependent upon a number of factors recognized by the art. These include, for example, compatibility with the chosen expression vector, toxicity of the plasminogen fragment to the cell, rate of transformation, expression characteristics, bio-safety, and costs. A balance of these factors must be struck with the understanding that not all hosts may be equally effective for the expression of a particular plasminogen fragment.

Eukaryotic host cells are preferred for making the plasminogen fragments of the invention. Within the above guidelines, useful eukaryotic host cells include yeast and other fungi, animal cell lines, animal cells in an intact animal, insect cells, and other eukaryotic host cells known in the art.

The host cells may be transformed with a vector comprising DNA encoding a plasminogen fragment of the invention. On the vector, the coding sequence must be operatively linked to expression control sequences.

As used herein "operatively linked" refers to the linking of DNA sequences in such a manner that the plasminogen fragment will be expressed. Preferably the linking, including the order of the sequences, the orientation of the sequences, and the relative spacing of the various sequences, is performed so that optimum expression is obtained.

The expression control sequences must include a promoter. The promoter used in the vector may be any sequence which shows transcriptional activity in the host cell and may be derived from genes encoding homologous or heterologous proteins and either extracellular or intracellular proteins. However, the promoter need not be identical to any naturally-occurring promoter. It may be composed of portions of various promoters or may be partially or totally synthetic. Guidance for the design of promoters is provided by studies of promoter structure such as that of Harley and Reynolds, *Nucleic Acids Res.*, 15, 2343–61 (1987). Also, the location of the promoter relative to the transcription start may be optimized. See Roberts, et al., *Proc. Natl Acad. Sci. USA*, 76, 760–4 (1979). The promoter may be inducible or constitutive, and is preferably a strong promoter. By "strong," it is meant that the promoter provides for a high rate of transcription in the host cell.

In the vector, the coding sequences must be operatively linked to transcription termination sequences, as well as to the promoter. The coding sequence may also be operatively linked to expression control sequences other than the promoters and transcription termination sequences. These additional expression control sequences include activators, enhancers, operators, stop signals, cap signals, polyadenylation signals, 5' untranslated sequences, and other sequences and signals involved with the control of transcription or translation.

The consensus sequence for the translation start sequence of eukaryotes has been defined by Kozak (*Cell*, 44, 283–292 (1986)) to be: C(A/G)CCAUGG. Deviations from this sequence, particularly at the −3 position (A or G), have a large effect on translation of a particular mRNA. Virtually all highly expressed mammalian genes use this sequence. Highly expressed yeast mRNAs, on the other hand, differ from this sequence and instead use the sequence (A/Y)A (A/U)AAUGUCU [SEQ ID NO:14] (Cigan and Donahue, *Gene*, 59, 1–18 (1987)). These sequences may be altered empirically to determine the optimal sequence for use in a particular host cell.

DNA coding for a plasminogen fragment of the invention may prepared using standard methods such as those described in Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989). In particular, clones coding for plasminogen are known. See, e.g., GenBank PCT application WO 95/29242; Browne et al., *Fibrinolysis*, 5, 257–260 (1991). Other clones may be identified by methods known in the art. The clones, whether known or newly-identified, may be modified to code for a plasminogen fragment of the invention by methods known in the art.

The coding sequences may, alternatively, be synthesized using standard techniques that are well known in the art using the known plasminogen sequences. For instance, DNA sequences may be synthesized by phosphoamidite chemistry in an automated DNA synthesizer, purified, annealed, ligated and cloned into suitable vectors. Chemical synthesis is preferable for several reasons.

First, chemical synthesis is desirable because codons preferred by the host in which the DNA sequence will be expressed may be used to optimize expression. Not all of the codons need to be altered to obtain improved expression, but greater than 50%, most preferably at least about 80%, of the codons should be changed to host-preferred codons. The codon preferences of many host cells are known. See *Maximizing Gene Expression*, pages 225–85 (Reznikoff & Gold, eds., 1986). The codon preferences of other host cells can be deduced by methods known in the art.

The use of chemically synthesized DNA also allows for the selection of codons with a view to providing unique or nearly unique restriction sites at convenient points in the sequence. The use of these sites provides a convenient means of constructing the synthetic coding sequences. In addition, if secondary structures formed by the messenger RNA transcript or other destabilizing sequences interfere with transcription or translation, they may be eliminated by altering the codon selections.

Chemical synthesis also allows for the use of optimized expression control sequences with the DNA sequence coding for a plasminogen fragment. In this manner, optimal expression of the plasminogen fragments can be obtained. For instance, as noted above, promoters can be chemically synthesized and their location relative to the transcription start optimized.

DNA coding for a signal or signal-leader sequence may be located upstream of the DNA sequence encoding the plasminogen fragment. A signal or signal-leader sequence is an amino acid sequence at the amino terminus of a protein which allows the protein to which it is attached to be secreted from the cell in which it is produced. Suitable signal and signal-leader sequences are well known. Although secreted proteins are often easier to purify, expression levels are generally lower than those that can be obtained in the absence of secretion.

Vectors for expressing the plasminogen fragments may be any vector which may conveniently be subjected to recombinant DNA procedures and which is capable of expressing a plasminogen fragment in the selected host cell. The vector used to transform the host cells may have one or more replication systems which allow it to replicate in the host cells. In particular, when the host is a yeast, the vector should contain the yeast 2u replication genes REP 1–3 and origin of replication.

Alternatively, an integrating vector may be used which allows the integration into the host cell's chromosome of the sequence coding for a plasminogen fragment of the invention. Although the copy number of the coding sequence in the host cells would be lower than when self-replicating vectors are used, transformants having sequences integrated into their chromosomes are generally quite stable.

When the vector is a self-replicating vector, it is preferably a high copy number plasmid so that high levels of expression are obtained. As used herein, a "high copy number plasmid" is one which is present at about 100 copies or more per cell. Many suitable high copy number plasmids are known.

The vector desirably also has unique restriction sites for the insertion of DNA sequences and a sequence coding for a selectable or identifiable phenotypic trait which is manifested when the vector is present in the host cell ("a selection marker"). If a vector does not have unique restriction sites, it may be modified to introduce or eliminate restriction sites to make it more suitable for further manipulations.

After the vector comprising a DNA sequence coding for a plasminogen fragment of the invention is prepared, it is used to transform the host cells. Methods of transforming host cells are well known in the art, and any of these methods may be used.

Transformed host cells are selected in known ways and then cultured under conditions effective to produce the plasminogen fragment. The methods of culture are those well known in the art for the chosen host cell.

The expressed plasminogen fragment may be recovered using methods of recovering and purifying proteins from recombinant cell cultures which are well known in the art. In particular, antibodies which bind selectively to the plasminogen fragments of the invention may be used to purify the fragments (see below).

The invention also provides methods of treating an angiogenic disease. An angiogenic disease is one caused by, involving or dependent on angiogenesis. Angiogenic diseases include neoplastic diseases (e.g., tumors and tumor metastasis), benign tumors (e.g., hemangiomas, acoustic neuromas, neurofibromas, trachomas, pyrogenic granulomas), connective tissue disorders (e.g., rheumatoid arthritis and atherosclerosis), ocular angiogenic diseases (e.g., diabetic retinopathy, retinopathy of prematurity, macular degeneration, corneal graft rejection, neovascular glaucoma, retrolental fibroplasia, rubeosis), cardiovascular diseases, cerebral vascular diseases, diabetes-associated diseases and immune disorders (e.g., chronic inflammation and autoimmunity).

The angiogenic disease may be treated by administering an effective amount of native angiostatin or of another plasminogen fragment having the N-terminal sequence of plasmin and containing at least a portion of kringle 5. Native angiostatin is preferred for the reasons given above.

The angiogenic disease may also be treated by administering an amount of a sulfhydryl donor sufficient to cause conversion of plasmin to angiostatin. An effective amount of a plasminogen activator may also be administered to the animal to produce plasmin from plasminogen. The plasminogen or plasmin may be those found endogenously in the animal or effective amounts of plasminogen or plasmin are also administered to the animal. Animals treatable according to the invention include mammals, such as dogs, cats, horses, other domestic animals, and humans.

Effective dosage forms, modes of administration and dosage amounts for the various compounds for treating angiogenic diseases may be determined empirically, and making such determinations is within the skill of the art. It is understood by those skilled in the art that the dosage amount will vary with the activity of the particular compound employed, the severity of the angiogenic disease, the route of administration, the rate of excretion of the compound, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day.

The compounds of the present invention may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). The preferred routes of administration are subcutaneous, orally and intravenously. The use of biodegradable polymers similar to that described by Brem, et al., *Lancet*, 345, 1571 (1995) for the local sustained release of pharmacological agents following incorporation into the biodegradable polymers is also a preferred method of administration. Implantation of the drug-impregnated polymer at, e.g., a tumor site, allows prolonged local exposure with minimal systemic exposure.

While it is possible for a compound of the present invention to be administered alone, it is preferable to administer the compound as a pharmaceutical formulation (composition). The pharmaceutical compositions of the invention comprise a compound of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, ophthalmic, topical, rectal, vaginal and/or parenteral administration. Regardless of the route of administration selected, the compounds of the present invention are formulated into pharmaceutically-acceptable dosage forms by conventional methods known to those of skill in the art.

The amount of active ingredient which will be combined with a carrier material to produce a single dosage form will vary depending upon the host being treated, the particular mode of administration and all of the other factors described above. The amount of active ingredient which will be combined with a carrier material to produce a single dosage form will generally be that amount of the compound which is the lowest dose effective to produce a therapeutic effect or the maximally-tolerated dose that yields a therapeutic increment for life-threatening illnesses, such as cancer.

Methods of preparing pharmaceutical formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound of the present invention as an active ingredient. A compound of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical compositions of this invention suitable for parenteral administrations comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

An angiogenic disease can also be treated by gene therapy. In particular, a transgene comprising DNA coding for a plasminogen fragment having the N-terminal sequence of plasmin and containing at least a portion of kringle 5 operatively linked to expression control sequences is administered to an animal suffering from such a disease. Preferably the plasminogen fragment coded for by the transgene is native angiostatin. The preparation of DNA coding for the plasminogen fragments of the invention, including native angiostatin, operatively linked to expression control sequences is described above. Expression of the transgene in the animal results in the production of the plasminogen fragment, which inhibits angiogenesis in the animal.

Methods and materials for gene therapy are well known in the art. See Culver, *Gene Therapy: A Primer for Physicians* (Revised 2nd ed., 1996), U.S. Pat. Nos. 5,521,291, 5,460,831 and 5,559,099, PCT applications WO 95/29242, WO 96/14876, and WO 96/35774, all of which are incorporated herein by reference in their entirety. See also, Kirshenbaum, et al., *J. Clin. Invest.*, 92, 381–387 (1993) and Drazner et al., *J. Clin. Invest.*, 99, 288–296 (1997). In particular, suitable methods and vehicles for delivery of transgenes are known and may be used to deliver the transgenes of the invention.

For instance, the transgene can be transfected into desired cells in vitro, and the transformed cells injected into an animal suffering from an angiogenic disease, preferably after expansion of the number of transformed cells. Methods of transfecting a transgene into cells in vitro are well known and include electroporation, direct injection of naked DNA into cells, particle bombardment, delivery by liposomes or other lipid-based carriers, delivery by viral vectors, etc.

Alternatively, the transgene can be administered to the animal in such a manner that it transforms cells within the animal. Methods of delivering transgenes in vivo are also well known and include direct injection of naked DNA into desired tissues, organs, or tumors, use of liposomes and other lipid-based carriers to deliver the transgene, use of a noninfectious viral vector (e.g., a replication-deficient adenoviral vector) to deliver the transgene, use of targeted vehicles (a vehicle that allows the vehicle to bind to, and deliver the transgene to, a specific cell, tissue, organ or tumor such as liposomes having a tumor-specific antibody attached to them) to deliver the transgene, etc.

The invention also provides antibodies which bind selectively to a plasminogen fragment of the invention, including antibodies which bind selectively to native angiostatin. "Binds selectively" means that the antibody binds to a plasminogen fragment of the invention, such as native angiostatin, in preference to plasminogen or plasmin.

Antibodies coming within the scope of the invention include polyclonal antibodies, affinity-purified antisera, monoclonal antibodies, fragments of antibodies (such as Fab, F(ab') or F(ab')$_2$) that are capable of binding antigen, any known isotype or subclass of antibody, and engineered antibodies (such a single-chain antibody prepared by recombinant DNA techniques). The only requirements are that the final antibody preparation have specificity for the plasminogen fragment and be capable of binding selectively to the fragment.

Methods of making antibodies and fragments of antibodies are well known in the art. For instance, the antibodies of the present invention may be prepared by injecting a suitable host animal (such as a rabbit, goat, horse or other mammal) with a plasminogen fragment of the invention in admixture with an adjuvant. The injections of the fragment are continued until an antiserum of suitable titer is obtained. The antiserum is harvested and may be further purified using known techniques if needed or desired. For instance, the antibodies may be affinity purified or may be fractioned such as by DE-52 chromatography.

Preferably, however, the antibodies of the invention are prepared by somatic cell hybridization by fusing cells from an immunized animal (such as rats, hamsters, mice or other mammal) with an immortal cell line such as myeloma cells. The fused cells are cloned, and monoclonal antibodies of appropriate specificity can be isolated by screening the cloned fused cells. Techniques of preparing monoclonal antibodies are well-known.

Antibodies which bind selectively to a plasminogen fragment of the invention can be used to purify the plasminogen fragments from fluids containing them. Such fluids include culture media, such as those resulting from practice of the methods of the invention for producing native angiostatin and the plasminogen fragments of the invention (see above). Native angiostatin would be found, in addition, in body fluids (e.g., blood, plasma, serum, saliva, urine and fluids produced by tumors).

To purify a plasminogen fragment, the fluid containing it is contacted with an antibody specific for the particular fragment. Preferably, the antibody is attached to a solid surface before being contacted with the fluid containing the fragment. Suitable solid surfaces are well known in the art and are available commercially. Examples include glass, polyacrylamide, polymethylmethacrylate, polycarbonate, polyacrylonitrile, polyethylene, polypropylene, polystyrene, latex beads, agarose beads, and nylon.

The antibody is preferably attached covalently to the solid surface. Methods and agents for attaching antibodies covalently to solid surfaces are well known in the art. Suitable agents include carbodiimide, cyanoborohydride, diimidoesters, periodate, alkylhalides, succinimides, dimethylpimelimidiate and dimaleimides. See Blair et al., *J. Immunol. Methods*, 59, 129 (1993); Blair et al., *Cancer Res.*, 41, 2700 (1981); Gautheier et al., *J. Expr. Med.*, 156, 766 (1982).

The specific concentrations of reactants, the temperature and time of incubation, as well as other conditions for obtaining binding of the antibody to the plasminogen fragment, can be varied depending on such factors as the concentration of the plasminogen fragment in the fluid, the nature of the fluid and the like. Those skilled in the art will be able to determine operative and optimal conditions while employing routine experimentation.

After the antibody has bound to the plasminogen fragment, the remainder of the fluid is separated from the bound plasminogen fragment. The plasminogen fragment is then released from the antibody by known methods.

Most preferably, a solid surface with the antibody attached to it is located in a column. For instance, a column filled with agarose beads having antibody attached to them. The fluid containing the plasminogen fragments is simply passed through the column, and the plasminogen fragments in the fluid bind to the antibody in the column and are retained in the column, while the remainder of the fluid passes through the column. After the column is washed, the plasminogen fragments are released from the antibody.

Antibodies of the invention which bind selectively to native angiostatin can also be used to detect or quantitate native angiostatin for the diagnosis of an angiogenic disease or to monitor for the recurrence of such a disease. Such antibodies can also be used to study the mechanism of action of angiostatin in the body.

Native angiostatin may be detected in materials such as body fluids (see above), cells and tissues (tumor tissue, placenta, uterus, brain, liver and intestines). Native angiostatin may be released from the cells or tissues by known extraction techniques, or intact cells or tissue sections may be used.

The native angiostatin in fluids or extracts can be detected or quantitated using conventional immunoassay techniques. Such techniques include agglutination, radioimmunoassay, enzyme immunoassays, fluorescence assays, calorimetric assays, etc. The immunoassay may be performed in the competitive binding format or may be an immunometric assay. It may be a homogenous or heterogenous assay. Suitable homogenous techniques are fluorescence quenching and enhancement, energy transfer immunoassay, double antibody steric hinderance immunoassay, substrate-labeled immunoassay, prosthetic group-labeled immunoassay and enzyme modulator-labeled immunoassay.

The native angiostatin on cells or tissues can be detected by standard immunohistochemical techniques well known in the art. For example, tumors are biopsied or collected, and tissue sections cut with a microtome to examine sites of native angiostatin production. Such information is useful for diagnostic and possibly therapeutic purposes in the detection and treatment of cancer and is useful for research purposes for studying the mode of action of angiostatin.

The native angiostatin can be detected or quantified using a labeled antibody which binds selectively to native angiostatin (primary antibody) or a labeled component that binds to immunoglobulin, such as another antibody (secondary antibody) or protein A. Suitable labels for either the primary antibody or for the component which binds to the primary antibody are well-known in the art. They include: 1) enzymes (e.g., horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase and acetylcholine esterase); 2) fluorophores (such as fluorescein isothiocyanate, rhodamine, phycoerythrin, phycocyanin, allophycocyanin, o-phtaldehyde and fluorescamine), 3) radionucleotides (such as $^{125}$I); 4) bioluminescent labels (such as luciferin, luciferase and aequorin); 5) chemiluminescent labels (such as luminol, isoluminol, aromatic acridinium ester, imidazole, acridinium salt and oxalate ester); 6) particulate lables (such as gold nanoparticles); and 7) biotin/avidin or biotin/streptavidin. The binding and detection of these labels can be performed using standard techniques known to those skilled in the art.

The specific concentrations of reactants, the temperature and time of incubation, as well as other conditions, can be varied in whatever immunoassay or immunohistochemical technique is employed, depending on such factors as the concentration of the native angiostatin in the sample, the nature of the sample and the like. Those skilled in the art will be able to determine operative and optimal conditions for each determination while employing routine experimentation.

A test kit for detecting or quantitating native angiostatin is also part of the invention. The kit is a packaged combination of one or more containers holding reagents useful in performing the immunoassays or immunohistochemical techniques of the invention. Suitable containers for the reagents of the kit include bottles, vials, test tubes, microtiter plates, dipsticks, strips, and other solid surfaces.

The kit will comprise a container of an antibody which binds selectively to native angiostatin. These antibodies are those described above. The antibody may be in solution, may be lyophilized, or attached to a solid surface, and may be labeled or unlabeled. The solid surfaces are the types described above, and the antibody is attached as described above.

The kit may further comprise a container holding the above-described labeled component that binds to the primary antibody. The labels are those described above.

Finally, the kit may also contain other materials which are known in the art and which may be desirable from a commercial and user standpoint. Such materials may include a sample of native angiostatin (for standardizing immunoassays or for binding to cells or tissues in immunohistochemical techniques), buffers, enzyme substrates, diluents, and equipment for performing the immunoassay or immunohistochemical technique.

EXAMPLES

Example 1

Preparation of Conditioned Medium Containing Plasminogen-Angiostatin Converting Activity (PACA)

This example demonstrates that a variety of cells express enzymatic activity that can generate bioactive angiostatin from purified human plasminogen or plasmin. Affinity-purified angiostatin generated by incubating plasminogen or plasmin with serum-free conditioned medium (SFCM) inhibited human endothelial cell proliferation, migration induced by angiogenic factor basic fibroblast growth factor (bFGF), endothelial cell tube formation, and bFGF-induced corneal angiogenesis. Serine proteinase inhibitors, but not inhibitors of metallo-, cysteine, or aspartic proteinases, blocked angiostatin generation. Elastatinal, a specific inhibitor of elastase, failed to block angiostatin generation, indicating that an elastase is not responsible for the conversion of plasminogen to angiostatin. Instead, the data show that serine proteinase activity is necessary for angiostatin generation.

A. Methods

1. Cell Culture. The human umbilical vein endothelial cells (HUVEC), were grown in RPMI supplemented with 20% bovine calf serum (Hyclone Laboratories Inc., Logan Utah #A-2151-L), 100 U/ml penicillin G, 100 mg/ml streptomycin, L-glutamine, (Gibco BRL), 2500 U Sodium heparin (Fisher Scientific, Itasca, Ill.), and 50 mg/ml endothelial cell growth supplement (Collaborative Biomedical Research, Bedford, Mass.). The other cells listed in Table 1 were grown in RPMI-1640 supplemented with 10% fetal bovine serum, 100 U/ml penicillin G, 100 mg/ml streptomycin (Gibco BRL, Gaithersburg, Md.). Cells were maintained at 37° C. in a humidified incubator in an atmosphere of 5% $CO_2$. To generate SFCM, confluent cell monolayers were washed twice with phosphate buffered saline, then serum-free RPMI was added. The next day the SFCM was collected and centrifuged at 3000 rpm for 15 minutes to remove insoluble cellular debris.

2. Angiostatin Generation. Two micrograms of human plasminogen, obtained by lysine-sepharose affinity chromatography of human plasma (Castellino & Powell, *Methods Enzymol,* 80, 365–78 (1981)), or human plasmin (#527624, Calbiochem-Novabiochem Corp., La Jolla, Calif.) were added to 100 μl aliquots of SFCM and the mixture incubated at 37° C. overnight. Aliquots were analyzed for angiostatin generation by western blot (see below). Plasminogen cleavage by SFCM was also assessed in the presence of proteinase inhibitors (Boehringer Mannheim, Indianapolis, Ind.).

3. Western Blot. Samples were electrophoresed under non-reducing conditions on 12% polyacrylamide gels (NOVEX, San Diego, Calif.) in Tris-Glycine running buffer (Laemmli, *Nature,* 227, 680–685 (1970)), and electrotransferred to a 0.45 μM polyvinylene difluoride (PVDF) membrane (Immobilon, Millipore, Bedford, Mass.). The membrane was then blocked for 30 minutes in blocking buffer (1% bovine serum albumin in Tris-buffered saline) and probed with a 1:1000 dilution of a monoclonal antibody to the kringles 1–3 (K1-3) fragment of human plasminogen (VAP 230L, Enzyme Research Laboratories, Inc., South Bend, Ind.). Following washing, the membrane was incubated for 30 minutes with an alkaline phosphatase conjugated goat anti-mouse IgG secondary antibody (Kirkegaard & Perry Laboratories (KPL), Gaithersburg, Md.) and developed using 5-bromo-4-chloro-3-indoyl-phosphate/nitroblue tetrazolium (KPL).

4. Zymographic Analysis. Zymograms to detect matrix metalloproteinase activity were performed as described previously. Heussen & Dowdle, *Anal. Biochem.,* 102, 196–202 (1980).

5. Chromogenic Peptide Substrates. To determine if an elastase was present, 50 μl of SFCM were incubated with 0.3 mM of chromogenic peptide substrates specific for elastase (substrate I, MeOSuc-Ala-Ala-Pro-Val-pNA [SEQ ID NO:15]; substrate II, Boc-Ala-Ala-Pro-Ala-pNA [SEQ ID NO:16]); substrate III, pGlu-Pro-Val-pNA; substrate IV, Suc-Ala-Ala-Pro-Abu-pNA) (Calbiochem-Novabiochem Corp.), at 37° C. for 2–18 hours. Substrate cleavage was determined by monitoring the absorbance at 405 nm (Molecular Devices, Menlo Park, Calif.).

6. Lysine-Sepharose Purification of Angiostatin. To generate purified angiostatin for bioactivity analyses, human plasminogen was incubated with PC-3 SFCM at 20 μg/ml overnight at 37° C. The reaction product was applied to a lysine-sepharose column (Pharmacia Biotech), pre-equilibrated with TBS (50 mM Tris, pH 7.5, and 150 mM NaCl) Following washes with TBS to remove non-specifically bound protein, angiostatin was eluted in 0.2 M epsilon aminocaproic acid (EACA) in TBS. The eluted fraction was dialyzed (molecular weight cut off 12,000–14,000) to phosphate buffered saline. To remove residual plasmin, the angiostatin was applied to a soybean trypsin inhibitor agarose (Sigma Chemical Co., St. Louis, Mo.) column, and the flow-through collected, filter-sterilized and stored at −80° C. until used. Angiostatin was quantitated by measuring the absorbance at 280 nm, using an $A^{1\%}/_{1\ cm}$ of 8.0. Sottrup-Jensen et al., in *Progress in Chemical Fibrinolysis and Thrombolysis,* vol. 3, pages 191–209 (Davidson et al. eds. 1978). The purified angiostatin was also examined by Coomassie brilliant blue staining of polyacrylamide gels, and immunodetection by western blot. Elastase-generated angiostatin, purified from human plasma as described in O'Reilly, et al., *Nature Med.,* 2, 689–692 (1996), was a generous gift from M. S. O'Reilly, Children's Hospital, Harvard University, Boston, Mass.

7. Microsequence Analysis of Angiostatin. To determine the $NH_2$-terminus of the angiostatin bands, 10 μg/ml of the affinity-purified angiostatin prepared by incubating plasminogen with PC-3 SFCM was electrophoresed on a 12% SDS-polyacrylamide gel, electroblotted to a PVDF membrane, and stained with Coomassie blue. The bands were excised, placed on Porton sample support discs, and sequenced using a pulse liquid-phase sequencer with phenylthiohydantoin analysis.

8. Endothelial Cell proliferation Assay. Cell proliferation was determined utilizing the CellTiter 96™ AQ Non-Radioactive Cell Proliferation Assay (Promega Corp., Madison, Wis.). The human endothelial cells were plated in a 96-well tissue culture plates (Becton Dickinson, Lincoln Park, N.J.) at a concentration of $5.0 \times 10^3$ cells/well. The following day, 1, 5, 8, or 10 μg/ml of angiostatin in fresh medium was added to triplicate wells. Wells without angiostatin served as control. The cells were incubated for 72 hours, and an absorbance read at 490 nm, reflecting the number of proliferating cells, was measured using an automated microplate reader (Molecular Devices). The results are reported as the percent of non-treated control cell number.

9. Endothelial Cell Migration Assay. To determine the ability of angiostatin prepared by incubation of plasminogen with PC-3 SFCM to block migration of endothelial cells towards an angiogenic factor, bFGF, migration assays were performed in a modified Boyden chamber using bovine capillary endothelial cells (a kind gift of Dr. Folkman, Harvard Medical School, Boston, Mass.) as described previously. Dameron et al., *Science,* 265, 1582–84 (1994). Cells were grown in Dulbecco's modified Eagle's medium (DMEM) with 10% donor calf serum and 100 mg/ml endothelial cell mitogen and used at passage 15. To assess migration, the cells were serum starved overnight in DMEM supplemented with 0.1% bovine serum albumin (BSA), harvested, suspended in DMEM/BSA, plated at $10^6$/ml on the lower surface of a gelatinized membrane (Nucleopore Corp., Plesanton, Calif.) in an inverted Boyden chamber, and incubated for 1.5–2 hours to allow cell attachment. The chambers were reinverted, test material was added to the top well, and the chamber incubated for an additional 3–4 hours. Membranes were then fixed and stained and the number of cells that migrated to the top of the filter in 10 high-power fields was determined. DMEM with 0.1% BSA was used as a negative control, and bFGF (provided by Dr. Noel Bouck and prepared as described in Dameron et al., *Science*, 265, 1582–1584 (1994)) at 10 ng/ml was used as a positive control.

10. Endothelial Cell Tube Formation. HUVEC were plated on gels of Matrigel (kindly provided by Hynda Kleinman, National Institute of Dental Research) in 24-well tissue culture plates as described previously. Schnaper et al., *J. Cell. Physiol*, 156, 235–246 (1993). Angiostatin, prepared by incubation with PC-3 SFCM, in non-conditioned RPMI was added to the wells, followed by cells at a final concentration of $4.0 \times 10^4$ cells in 1 ml of 50% HUVEC culture medium, 50% RPMI. Each angiostatin or control condition was assayed in triplicate. The cultures were incubated for 16–18 hours at 37° C., in a 5% $CO_2$ humidified atmosphere, then fixed with Diff-Quick Solution II (Baxter, McGraw Park, Ill.). A representative area of the tube network was photographed using a Polaroid MicroCam camera at a final magnification of 35×. The photographs were then quantitated by a blinded observer who measured the length of each tube, correcting for portions of tubes that were incomplete. The total length of the tubes was determined for each photograph and the mean tube length was determined. The results were expressed as the mean±standard error of the mean.

11. Corneal Angiogenesis Assay. The corneal assay was performed as described previously. Polverini et al., *Methods Enzymol*, 198, 440–450 (1991). Briefly, 5 µl hydron pellets (Hydron Laboratories, New Brunswick, N.J.) containing 10 µg/ml bFGF or bFGF plus 1 or 10 µg/ml angiostatin were implanted into the cornea of anesthetized rats. After 7 days, the animals were sacrificed and corneal vessels were stained with colloidal carbon and corneas were examined for angiogenic activity.

B. Results

1. Angiostatin Generation By Conditioned Culture Medium. Incubation of human plasminogen with the SFCM produced by PC-3 cells resulted in the generation of multiple immunoreactive bands at approximately 50 kD (FIG. 1A), similar to those observed by O'Reilly et al. *Cell*, 79, 315–328 (1994). Examination of SFCM from additional cell lines also revealed the generation of the multiple bands, similar to the PC-3 SFCM (data not shown). These cell lines are listed in Table 1 below.

The initial indication that the product was angiostatin was based on the immunoreactivity with the monoclonal antibody specific for kringles 1–3 (K1–3) of plasminogen and the size of the cleavage product. Subsequent confirmation that the plasminogen cleavage product was bioactive angiostatin is described below.

Figure 1A:
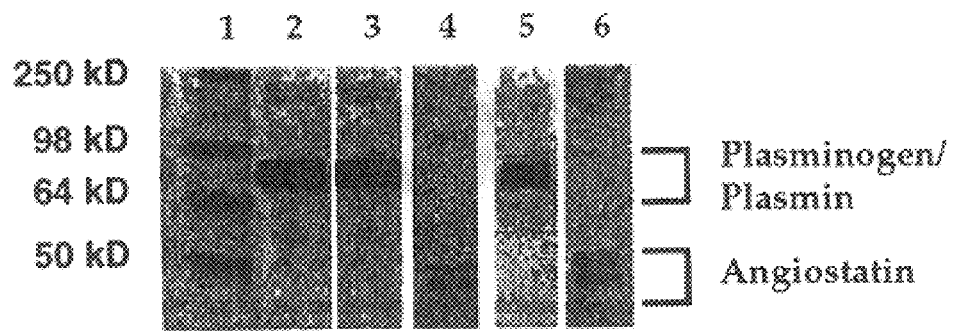
FIG. 1A: Western blot showing conversion of plasminogen and plasmin to angiostatin by serum-free conditioned medium (SFCM) produced by PC-3 cells. Lane 1, molecular weight standard; lane 2, human plasminogen; lane 3, human plasminogen incubated overnight at 37° C. in non-conditioned RPMI; lane 4, human plasminogen incubated overnight at 37° C. in SFCM from PC-3 cells; lane 5, human plasmin incubated in non-conditioned RPMI; lane 6, human plasmin incubated in SFCM produced by PC-3 cells.
Figure 1B:
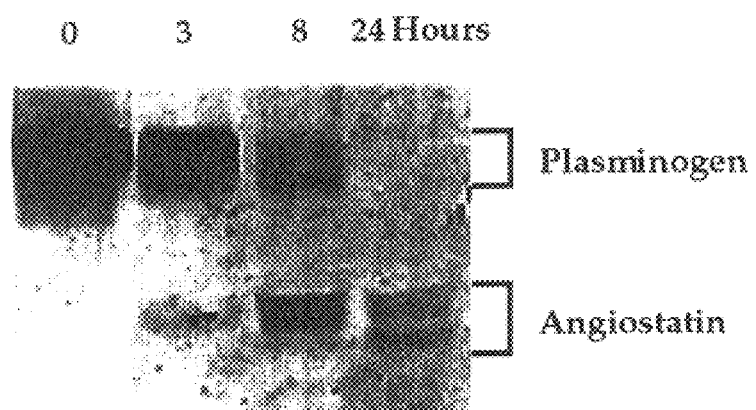
FIG. 1B: Western blot showing that the generation of angiostatin from plasminogen was time dependent. PC-3 SFCM was incubated with plasminogen and, at the time-points indicated, aliquots were removed and snap frozen prior to western blot analysis. Trace generation of angiostatin was first observed at 3 hours, and complete conversion was noted at 24 hours.
Figure 1C:
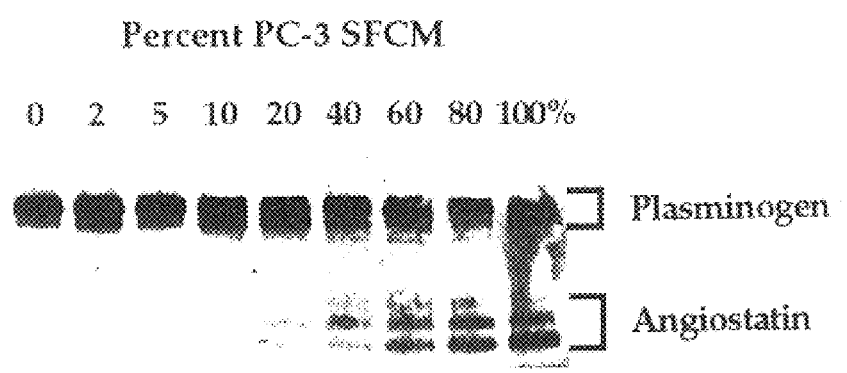
FIG. 1C: Western blots showing that the generation of angiostatin by PC-3 SFCM was concentration dependent. SFCM was diluted with various amounts of fresh RPMI as indicated and incubated with plasminogen for 24 hours.
Figure 1D:
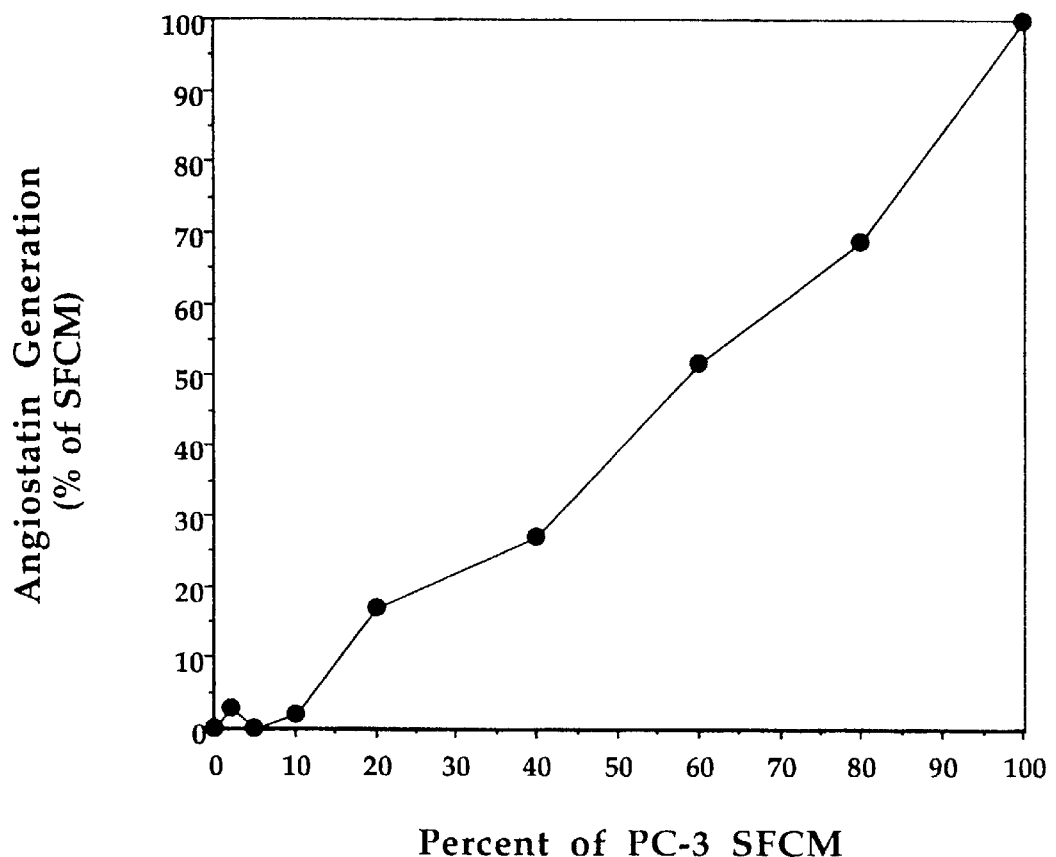
FIG. 1D: Graph illustrating the relationship of angiostatin generation to the amount of SFCM. The relative angiostatin signal was quantitated by scanning densitometer with background subtraction. At 18 hours incubation, there was a linear relationship between the amount of angiostatin generated and the amount of PC-3 SFCM present in the reaction mixture.

Angiostatin generation by PC-3 SFCM was time-dependent. There was a significant decrease in the plasminogen substrate and a corresponding increase in angiostatin beginning at 3 hours, with complete conversion to angiostatin by 24 hours (FIG. 1B). Dilution of the PC-3 SFCM resulted in a proportional decrease in angiostatin generation (FIGS. 1C and 1D).

To determine whether plasmin, the activated form of the zymogen plasminogen, could also be converted to angiostatin, plasmin was evaluated as a potential substrate. Incubation of plasmin with PC-3 SFCM yielded a product indistinguishable from the plasminogen-derived angiostatin (FIG. 1A). In kinetic studies, plasmin was converted to angiostatin at a comparable rate to the plasminogen; 50% conversion by 8 hours, with complete conversion by 24 hours (data not shown). These data suggest that in vitro both plasminogen and plasmin are substrates from which angiostatin can be generated.

TABLE 1

Cell Lines Tested for Angiostatin-Generating Activity

|  | Activity |
|---|---|
| Human Prostate Carcinoma | |
| PC-3 | +++ |
| DU-145 | ++ |
| Ln-CaP | + |
| Human Breast Carcinoma | |
| MDA-MB-231 | ++ |
| MCF-7 | +/− |
| Human Glioma | |
| U-373 | + |
| U-118 | + |
| A-172 | ++ |
| U-87 | + |
| Mouse Melanoma | |
| B16F10 | ++ |
| Bovine Smooth Muscle | |
| Primary cell line | ++ |
| Bovine Aortic Endothelial Cells | |
| BAEC | ++ |

2. Enzymatic Class Of Plasminogen-Angiostatin Converting Activity. To determine the proteolytic class of the angiostatin generating activity, PC-3 SFCM was incubated with plasminogen in the presence of various proteinase inhibitors. The proteinase inhibitors were added to the SFCM/plasminogen mix prior to the overnight incubation. Samples were analyzed by western blot for evidence of inhibition of angiostatin generation.

Only serine proteinase inhibitors blocked angiostatin generation (see Table 2 below). By contrast none of the other classes of proteinase inhibitors were effective.

Angiostatin can be generated in vitro by limited proteolysis of plasminogen by elastase. Sottrup-Jensen et al. in *Progress in Chemical Fibrinolysis and Thrombolysis*, 3, 191–209 (Davidson et al. eds. 1978); O'Reilly et al., *Nature Med.*, 2, 689–692 (1996); Dong et al., *Proc. Am. Assoc. Cancer Res.*, 37, 58 (1996). In the present study, angiostatin generation was not inhibited by elastatinal, a specific inhibitor of elastase (see Table 2 below). Additionally, no elastase activity was detected in PC-3 SFCM based on co-incubation of SFCM with 4 elastase-sensitive chromogenic substrates for 24 hours (data not shown). These data indicate that the human plasminogen-angiostatin converting activity is unlikely to depend on the action of an elastase. Furthermore, gelatin zymograms revealed no evidence of active or latent metalloproteinases in the PC-3 SFCM (not shown).

TABLE 2

| Proteinase Inhibitor | Concentration | Class | Inhibitory Activity |
| --- | --- | --- | --- |
| Pefabloc | 4.0 mM | Serine Proteinases | Complete |
| Aprotinin | 0.3 µM | Serine Proteinases | Complete |
| Soybean Trypsin Inhibitor | 2.0 mM | Serine Proteinases | Complete |
| Benzamidine | 1–10 mM | Serine Proteinases | Weak |
| Elastatinal | 50–100 µM | Elastase | None |
| Antipain dihydrochloride | 100 µM | Limited Serine Proteinases | None |
| Leupeptin | 100 µM | Serine and Thiol Proteinases | None |
| Chymostatin | 100 µM | Chymotrypsin | None |
| Bestatin | 10 µM | Aminopeptidases | Weak |
| E-64 | 10 µM | Cysteine Proteinases | None |
| Pepstatin | 1.0 µM | Aspartic Proteinases | None |
| EDTA | 1–10 mM | Metalloproteinases | None |
| 1-10 Phenanthroline | 10 µM | Metalloproteinases | None |
| Phosphoramidon | 100 µM | Metalloproteinases | None |

*Complete inhibition is defined as no immunoreactive angiostatin bands; weak inhibition results in the development of faint angiostatin immunoreactive bands; and none refers to the full generation of angiostatin.

Figure 2:
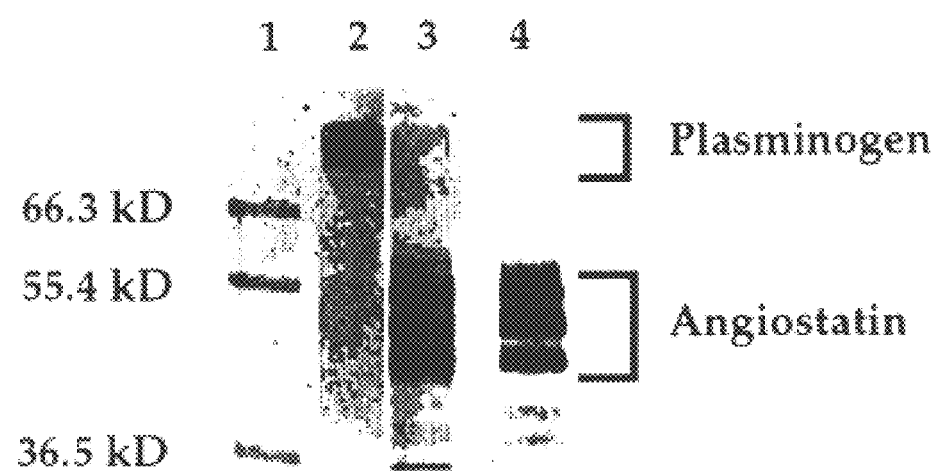
FIG. 2: Western blots after affinity purification of angiostatin generated by incubation of plasminogen with SCFM produced by PC-3 cells. Lane 1, molecular weight standards; lane 2, human plasminogen incubated overnight at 37° C. in non-conditioned RPMI; lane 3, angiostatin produced by incubation of plasminogen with PC-3 SCFM and then affinity purified on lysine-sepharose and detected on western blot by staining with Coomassie blue; lane 4, angiostatin produced by incubation of plasminogen with PC-3 SCFM and then affinity purified on lysine-sepharose and detected on western blot using the monoclonal antibody K1-3 to kringles 1-3.

3. Purification Of Angiostatin. Angiostatin generated by PC-3 SFCM was affinity purified on lysine-sepharose (O'Reilly et al., Nature Med., 2, 689–692 (1996)), and the resulting product examined by western blot and Coomassie blue staining (FIG. 2). The amino-terminal sequence of all three bands was KVYLSECKTG [SEQ. ID NO:1] that corresponds to residues 78–87 of the plasminogen molecule, confirming that the product was an internal fragment of plasminogen.

4. Angiostatin Generated By PC-3 SFCM Inhibits Angiogenesis. Because angiogenesis represents a cascade of cellular processes that includes endothelial cell proliferation, migration, and tube formation, (Folkman & Shing, J. Biol. Chem, 267, 10931–10934 (1992)), multiple in vitro and in vivo assays related to angiogenesis were utilized to confirm that the product generated by incubating plasminogen with PC-3 SFCM was bioactive angiostatin.

Figure 3A:
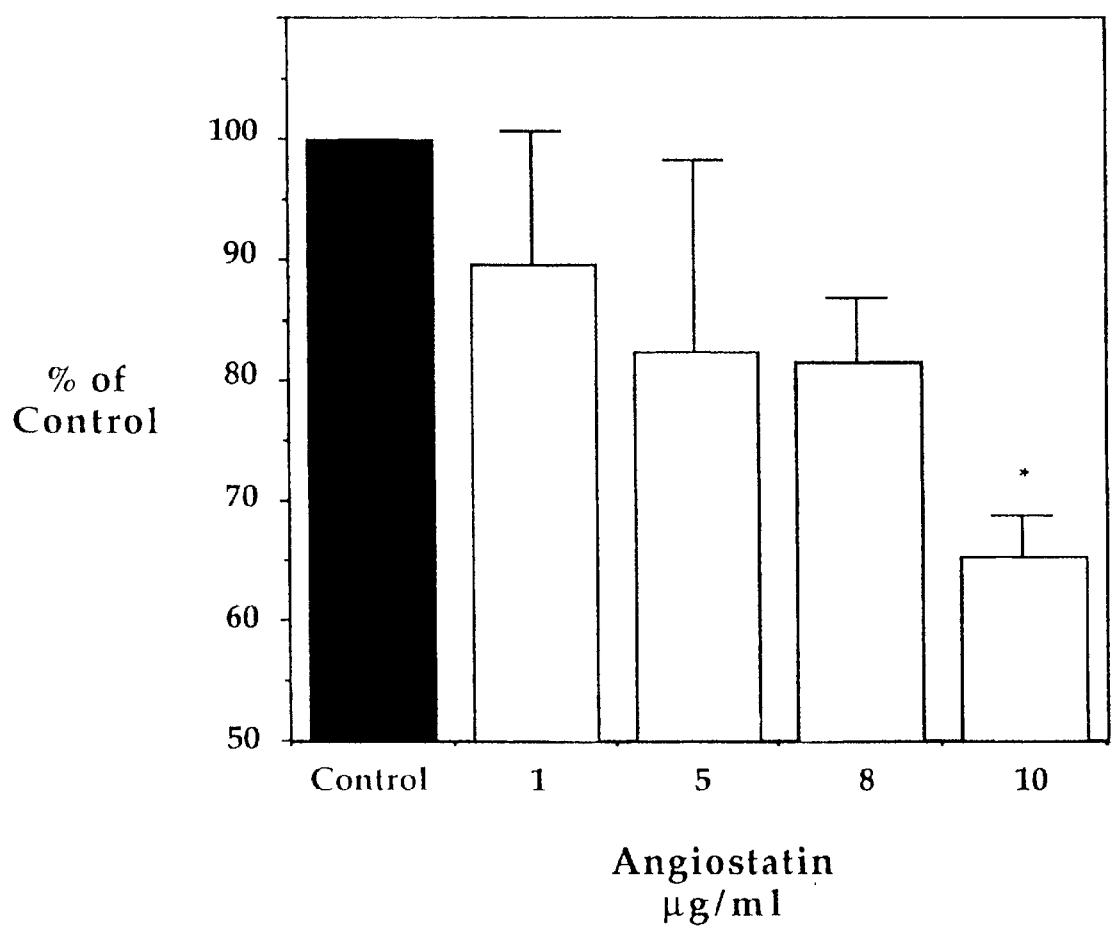
FIGS. 3A–B: Graphs showing that angiostatin produced by incubating plasminogen with PC-3 SCFM inhibits in vitro steps critical for angiogenesis.

Affinity purified angiostatin generated by PC-3 SFCM inhibited human endothelial cell proliferation in a concentration-dependent manner, with significant inhibition observed at 10 µg/ml ($P<0.05$) in comparison to the non-treated control cell proliferation (FIG. 3A).

Figure 3B:
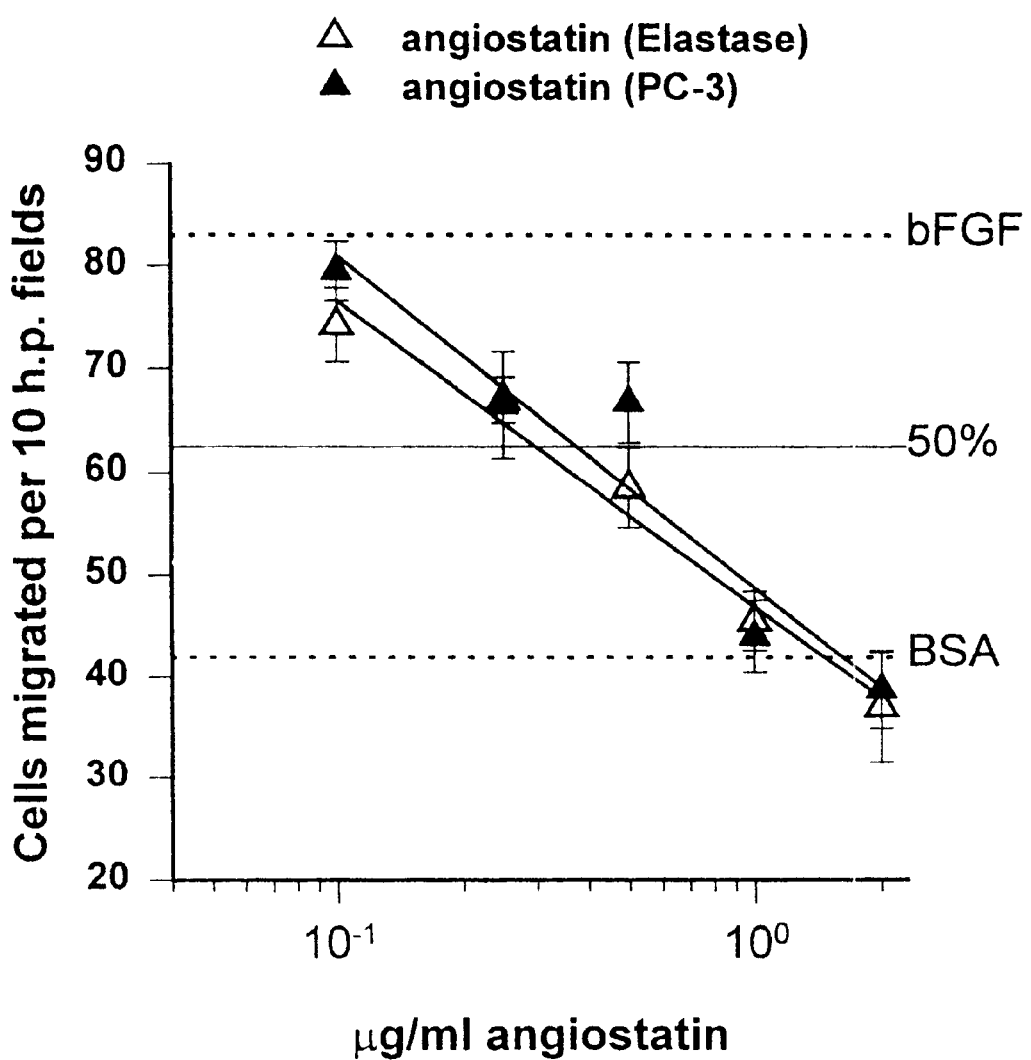

Angiostatin generated by PC-3 SFCM also inhibited the bFGF-induced migration of bovine capillary endothelial cells (FIG. 3B) with an $ED_{50}$ of 0.35 µg/ml. The dose/response curve of angiostatin generated by PC-3 SFCM was indistinguishable from that of elastase-generated angiostatin. Inhibition of migration occurred at a 10-fold lower concentration than required to inhibit proliferation, a finding that has been reported for other inhibitors of angiogenesis. Takano et al., Cancer Res., 54, 2654–2660 (1994). This may be due to the fact that the proliferation assay, in contrast to the migration assay, was conducted in RPMI supplemented with 20% calf serum and endothelial cell growth supplement, and therefore contained multiple stimulatory factors.

Figure 4A:
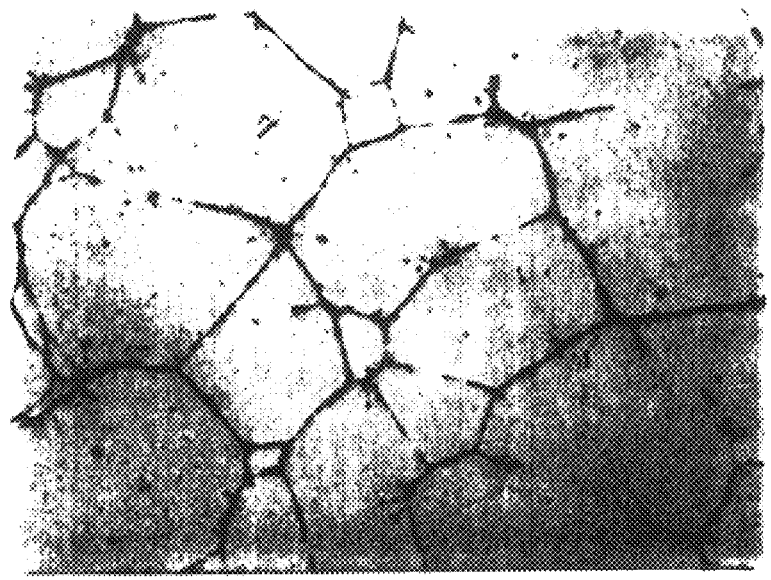
FIGS. 4A–B: Photographs showing that angiostatin produced by incubating plasminogen with PC-3 SCFM inhibits human endothelial cell tube formation in vitro. Human umbilical vein endothelial cells (HUVEC) were plated on gels of Matrigel in 24-well dishes and then were treated with 15 μg/ml of angiostatin produced using PC-3 SFCM in non-conditioned RPMI.
Figure 4B:
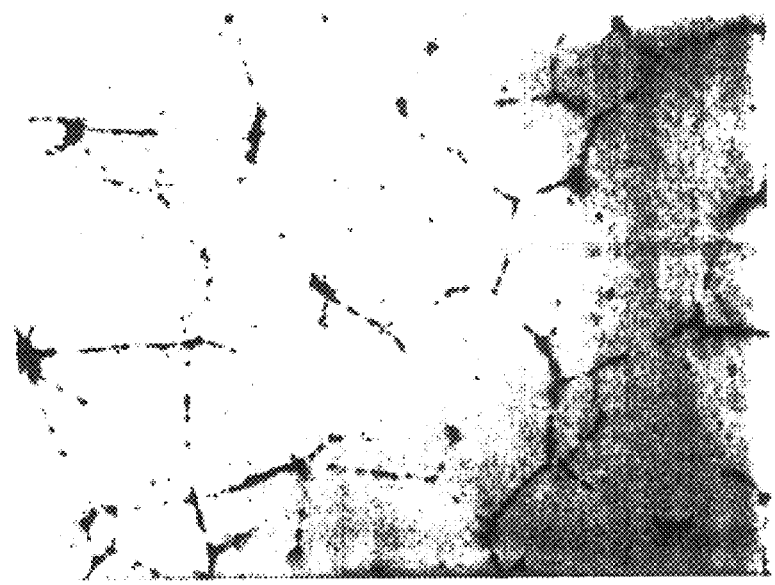

Endothelial cell tube formation on Matrigel was significantly inhibited at 15 µg/ml (FIGS. 4A and B); the mean length of tubes in non-treated control was 674.5±54 mm in comparison to angiostatin produced by PC-3 SFCM, 287.7±47 mm ($P<0.005$).

To determine the effect of angiostatin generated by PC-3 SFCM on corneal angiogenesis in vivo, its ability to block bFGF-induced angiogenesis in the corneal angiogenesis assay was tested. The bFGF pellet induced angiogenesis in 100% of implanted corneas (FIG. 5A). In contrast, angiostatin at 10 µg/ml completely inhibited the bFGF-induced angiogenic response in 3 of 3 animals (FIG. 5B). At a lower dose of 1.0 µg/ml, angiostatin completely blocked angiogenesis in 2 of 3 animals, with partial inhibition in the third animal.

Taken together, these data indicate that the angiostatin generated by the PC-3 SFCM is a potent inhibitor of both in vitro and in vivo angiogenesis.

Example 2

Identification of Factors Responsible for Converting Plasminogen to Angiostatin

The human prostate carcinoma cell line PC-3 was grown and PC-3 SFCM was prepared as described in Example 1. Angiostatin was generated by incubation with PC-3 SFCM or other materials identified below as described in Example 1. Western blots were performed as described in Example 1.

Figure 6:
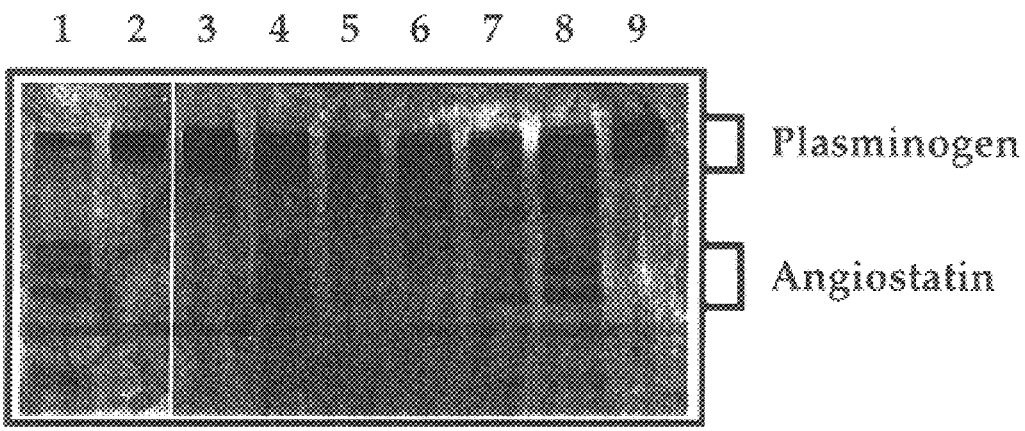
FIG. 6: Western blot showing that the batch eluate from Reactive Red 120-Agarose generates angiostatin when combined with Reactive Red 120-Agarose flow-through, RPMI or RPMI amino acids. Lane 1—SFCM+plasminogen; Lane 2—Reactive Red 120-Agarose flow-through+plasminogen; Lane 3—Reactive Red 120-Agarose batch eluate after dialysis to TBS+plasminogen; Lane 4—dialyzed batch eluate+Reactive Red 120-Agarose flow-through+plasminogen; Lane 5—dialyzed batch eluate+RPMI+plasminogen; Lane 6—dialyzed batch eluate+RPMI vitamin mix+plasminogen; Lane 7—dialyzed batch eluate+RPMI amino acid mix+plasminogen; Lane 8—dialyzed batch eluate+RPMI vitamin mix and amino acid mix+plasminogen; Lane 9—plasminogen+unconditioned RPMI.

PC-3 SFCM was applied to a Reactive Red 120-Agarose column (Sigma Chemical Co.). The flow-through had no residual plasminogen-angiostatin generating activity (PACA) as demonstrated by western blot analysis (FIG. 6). The bound material was eluted with 1 M KCl according to the manufacturer's protocol, then dialyzed to Tris-buffered saline (TBS, 20 mM Tris, pH 7.4, 100 mM NaCl), with a molecular cut-off of 6000–8000 Dalton. PACA was not detected in the dialyzed fraction (FIG. 6). The observation that PACA was not detected in either the flow-through or the eluate led to the hypothesis that two or more factors are necessary to generate angiostatin from plasminogen or plasmin, and that the factors were separated by the Reactive Red 120-Agarose chromatography, with one or more factors being present in the elaute and one more factors being contained in the flow-through.

To test this hypothesis, the dialyzed eluate was recombined with the flow-through. The recombined materials were able to convert plasminogen into angiostatin. Supplementation of the eluate with fresh RPMI culture medium, as well as the Reactive Red 120-Agarose flow-through, restored the capacity of the eluate to generate angiostatin, suggesting that the necessary factor was a component of RPMI, and not a protein or other factor unique to the SFCM.

To further define the putative cofactor, the individual components of RPMI were evaluated for the ability to complement the Reactive Red 120-Agarose eluate. The cofactor was present in the RPMI amino acid mix (FIG. 6).

To determine which amino acid was capable of restoring PACA to the Reactive Red 120-Agarose eluate, the 20 amino acids found in RPMI were tested individually. L-cysteine was the only amino acid capable of restoring PACA to the Reactive Red 120-Agarose eluate (data not shown).

Because the addition of L-cysteine to the Reactive Red 120-Agarose eluate restored angiostatin generating activity, it was hypothesized that the cofactor was a sulfhydryl donor. Pharmacological reducing agents, D-penicillamine and captopril were therefore examined for the ability to restore PACA to the Reactive Red 12-agarose eluate. Addition of 100 µM D-penicillamine to the Reactive Red 120-Agarose eluate restored angiostatin generating activity. Captopril also restored angiostatin generating activity to the Reactive Red 120-Agarose eluate.

PC-3 SFCM was diluted to 50 mM Tris, pH 10.0, 20 mM NaCl and applied to a Hi-Q Sepharose anion exchange resin (Bio Rad). No PACA was detected in the flow-through.

Preliminary experiments indicated that PACA eluted from the Hi-Q Sepharose column with 300 mM NaCl. Therefore, the bound material was eluted utilizing a linear gradient from 20 mM to 300 mM NaCl. PACA and urokinase-type plasminogen activator (u-PA) activity were measured in the fractions (after dilution to restore physiological NaCl concentrations). The u-PA activity and PACA co-purified (FIG. 7). Examination of the Reactive Red 120-Agarose eluate revealed it also contained u-PA.

As noted in Example 1, the $NH_2$-terminal cleavage of angiostatin is at $Lys^{77}$, a site that results from cleavage of Glu-plasminogen by plasmin. This suggests that plasmin generation may be a necessary intermediate step in angiostatin generation from plasminogen.

Figure 8:
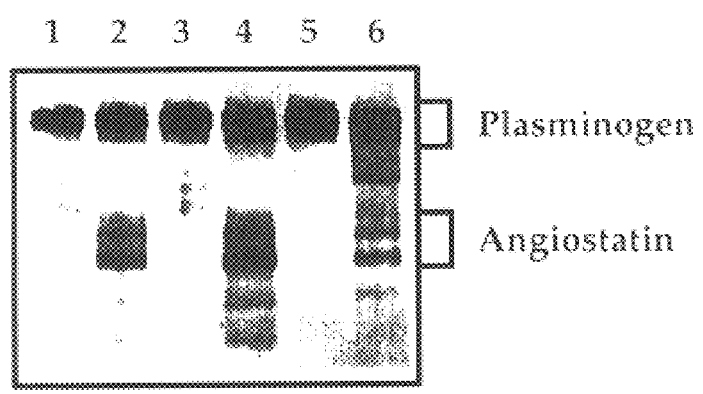
FIG. 8: Western blot showing that addition of u-PA and plasminogen to boiled Reactive Red 120-Agarose flow-through or fresh RPMI medium generated angiostatin. Lane 1—Reactive Red 120-Agarose flow-through+plasminogen; Lane 2—Reactive Red 120-Agarose flow-through+plasminogen+u-PA; Lane 3—Reactive Red 120-Agarose boiled flow-through+plasminogen; Lane 4—Reactive Red 120-Agarose boiled flow-through+plasminogen+u-PA; Lane 5—unconditioned RPMI+plasminogen; Lane 6—unconditioned RPMI+plasminogen+u-PA.

To determine if the factor in the Reactive Red 120-Agarose eluate was u-PA, u-PA was tested as a substitute for the Reactive Red 120-Agarose eluate. As illustrated in FIG. 8, u-PA was capable of generating angiostatin in the presence of boiled Reactive Red 120-Agarose flow-through or RPMI, both sources of sulfhydryl donors. This indicates that the only protein necessary for conversion of plasminogen to angiostatin is u-PA.

Figure 9:
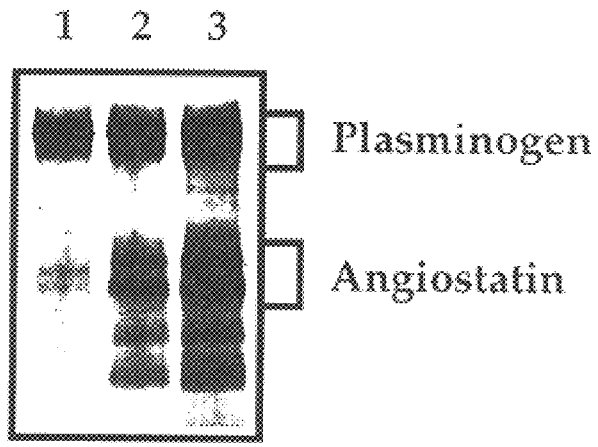
FIG. 9: Western blot showing that the Reactive Red 120-Agarose flow-through produces angiostatin in the presence of plasminogen activators. Lane 1—Reactive Red 120-Agarose flow-through+plasminogen; Lane 2—Reactive Red 120-Agarose flow-through+plasminogen+u-PA; Lane 3—Reactive Red 120-Agarose flow-through+plasminogen+t-PA.

Next, u-PA, tissue-type plasminogen activator (t-PA), and streptokinase were tested in combination with the Reactive Red 120-Agarose flow-through for PACA. The plasminogen activators alone failed to generate angiostatin from plasminogen but, in the presence of the flow-through, angiostatin was produced (FIG. 9). These data suggest that plasmin generation is an intermediate for angiostatin generation, and that angiostatin generation is not dependent on which plasminogen activator is present.

Example 3

Generation of Angiostatin Using Plasminogen Activators and Sulfhydryl Donors Having demonstrated that the only protein necessary for conversion of plasminogen to angiostatin is a plasminogen activator and that a sulfhydryl donor is a necessary cofactor, it was next determined if these components are sufficient for angiostatin generation. All incubations were performed at 37° C. for 18 hours in TBS, and the resulting samples were analyzed for angiostatin by Western blot (performed as described in Example 1).

Figure 10:
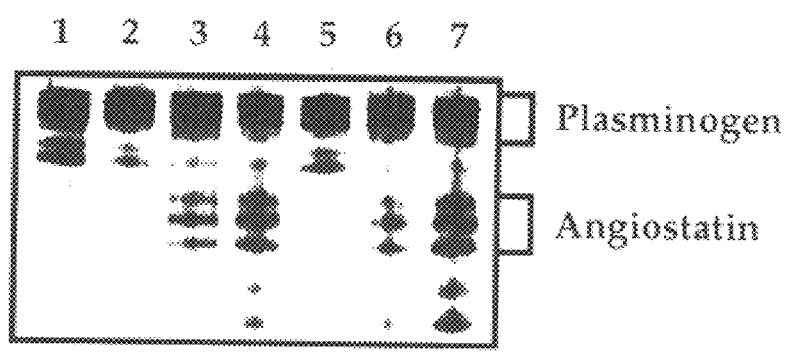
FIG. 10: Western blot showing the production of angiostatin by u-PA and glutathione. Lane 1—plasminogen+u-PA; Lane 2—plasminogen+u-PA+5 μM glutathione; Lane 3—plasminogen+u-PA+50 μM glutathione; Lane 4—plasminogen+u-pA+100 μM glutathione; Lane 5—plasminogen+u-PA+boiled 5 μM glutathione; Lane 6—plasminogen+u-PA+boiled 50 μM glutathione; Lane 7—plasminogen+u-PA+boiled 100 μM glutathione.

Incubation of u-PA with plasminogen and at least 5 $\mu$M reduced glutathione produced angiostatin (FIG. 10). No angiostatin was produced in the absence of the glutathione.

Figure 11:
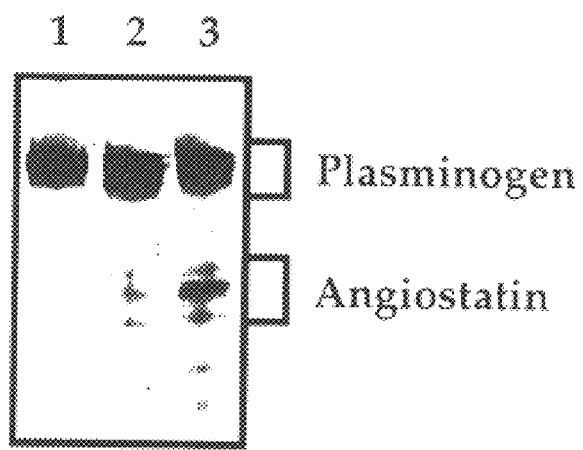
FIG. 11: Western blot showing that the combination of u-PA and D-penicillamine produces angiostatin. Lane 1—plasminogen+100 μM D-penicillamine; Lane 2—plasminogen+u-PA+100 μM D-penicillamine; Lane 3—plasminogen+u-PA+1.0 mM D-penicillamine.

Use of 100 $\mu$M or 1 mM D-penicillamine in combination with u-PA was also capable of generating angiostatin (FIG. 11).

Finally, incubation of plasminogen (0.2 $\mu$M) with u-PA (0.2 nM), t-PA (1.0 nM), or streptokinase (8.0 nM) with 100 $\mu$M N-acetyl-L-cysteine resulted in the production of angiostatin (FIG. 12). Plasminogen was not converted to angiostatin in the absence of N-acetyl-L-cysteine.

These data show that plasminogen is converted to angiostatin by each of the classic plasminogen activators in the presence of a sulfhydryl donor, but not in the absence of the sulfhydryl donor. Further, these data and the data in Example 2 demonstrate that angiostatin is produced in the presence of physiological (L-cysteine, reduced glutathione) and pharmacological (captopril, D-penicillamine, N-acetyl-L-cysteine) reducing agents.

Example 4

Use of Plasmin for Angiostatin Generation

Two micrograms of human plasminogen in 100 $\mu$l of TBS was incubated with 10 $\mu$l of uPA-Sepharose (Calbiochem, La Jolla, Calif.) for 2 hours at 37° C. Following this incubation, the sample was centrifuged to sediment the uPA-Sepharose, and the supernatant containing plasmin was collected. The complete conversion of plasminogen to plasmin was confirmed by analysis of the supernatant on Coomassie-stained reduced polyacrylamide gels. The purified plasmin was then incubated for 18 hours at 37° C. with 100 $\mu$M N-acetyl-L-cysteine, and samples analyzed for angiostatin generation by Western blot (performed as described in Example 1).

The results are shown in FIG. 13. These results demonstrate that plasmin is a necessary intermediate in the generation of angiostatin from plasminogen, and that angiostatin can be produced by incubation of purified plasmin with a sulfhydryl donor.

Example 5

Treatment of Tumors In Vivo with Sulfhydryl Donor, with and without Plasminogen Activator Eleven female beige nude mice (Taconic Labs, Germantown, N.Y.) 6–8 weeks of age were injected subcutaneously in the right flank with $1.0 \times 10^6$ murine hemangioendothelioma (EOMA) cells (generously provided by Dr. Robert Auerbach, Madison, Wis.) in 100 $\mu$l phosphate-buffered saline. The EOMA tumor cells were grown in Dulbecco's Modified Eagle Medium (DMEM) supplemented with 10% fetal bovine serum (FBS), 100 units/ml penicillin G, and 100 mg/ml streptomycin (Life Technologies Inc., Gaithersburg, Md.) and maintained at 37° C. in a humidified incubator in an atmosphere of 10% $CO_2$. The day of injection of the tumor cells was designated day 0.

Begining on day 1, each of the mice was injected subcutaneously twice a day with the following:

| Group And Number Of Mice | Treatment |
| --- | --- |
| Control (5) | Saline |
| NAC (4) | N-acetyl-L-cysteine in saline (6 mg per injection) |
| uPA + NAC (4) | urokinase - type plasminogen activator in saline (250 Units per injection) + N-acetyl-L-cysteine in saline (6 mg per injection) |

The size of the primary tumor in each mouse was measured three times weekly using tissue calipers, and tumor volume was determined using the formula (width$^2$×length× 0.52) (O'Reilly et al., Nature Medicine, 2, 689–692 (1996)). The results are presented in FIG. 14. As can be seen both treatment with NAC and treatment with uPA+NAC effectively and significantly decreased the mean tumor size as compared to the control group. It should be noted that one control mouse died on day 10 and another control mouse died on day 17. None of the mice treated with NAC or uPA+NAC died during the 21-day duration of the experiment.

Plasma samples taken from two of the control mice and three of the NAC-treated mice on the day of sacrifice were assayed for angiostatin by Western blot (performed as described in Example 1). As a control, two mice were injected subcutaneously with 1.00 mg of affinity-purified, cell-free angiostatin twice a day beginning on day 1 until 24 hours prior to sacrifice. Affinity-purified, cell-free angiostatin was generated as described in Example 3 and affinity purified on a lysine-sepharose column as described in Example 1. The results are shown in FIG. 15. As can be seen, administration of NAC to the mice caused the production of angiostatin in vivo (Lanes 5, 6 and 7). No angiostatin production was detected in control mice (Lanes 1 and 2).

Example 6

Determination of the C-Terminal Sequence of Native Angiostatin

Native angiostatin was generated by incubating human plasminogen (0.2 μM) with recombinant human u-PA (0.2 nM) (Abbott Laboratories, North Chicago, Ill.) and 100 μM N-acetyl-L-cysteine at 37° C. overnight. The material was then applied to a lysine-sepharose column (see Example 1), and the flow-through material was collected and concentrated. Aliquots of the concentrated flow-through material were electropheresed under non-reducing conditions on 12% polyacrylamide gels (NOVEX, San Diego, Calif.) in Tris-Glycine running buffer, electrotransferred to a 0.45 μm polyvinylene difluoride (PVDF) membrane (Immobilon, Millipore, Bedford, Mass.), and proteins stained with Coomassie blue.

The stained membrane showed two very prominent bands from the flow-through at approximately 30 kD. Although other bands were observed, the staining of these bands was considerably less than the staining of the two 30 kD bands, indicating that the two 30 kD bands contained the predominant constituents of the flow-through.

The N-terminal sequences of the proteins in the two 30 kD bands were determined by microsequence analysis as described in Example 1. The N-terminal sequence of the most prominent of the two bands was Lys Leu Tyr Asp Tyr Cys Asp Val [SEQ ID NO:2], while the sequence of the other band was Leu Tyr Asp Tyr Cys Asp Val [SEQ ID NO:3]. The location of these sequences in kringle 5 of plasminogen (see FIG. 16) and the prominence of the two bands provided extremely strong evidence that these were the fragments released as a result of the cleavage of plasminogen to form the C-terminal of native angiostatin. From the N-terminal sequences of the two 30 kD fragments, it was deduced that the C-terminal sequence of the native angiostatin was Cys Tyr Thr Thr Asn Pro Arg [SEQ ID NO:4] or Cys Tyr Thr Thr Asn Pro Arg Lys [SEQ ID NO:5]. These C-terminal sequences would be formed by cleavage after amino acid 529 (Arg) or 530 (Lys) of human plasminogen, which is in kringle 5 (see FIG. 16), which are known plasmin cleavage sites. Cleavage at this point would give a plasminogen fragment of about the molecular weight observed for native angiostatin on polyacrylamide gel electrophoresis under non-reducing conditions (50–60 kD).

The N-terminal sequence of human native angiostatin [SEQ ID NO:1] is given above in Example 1. Thus, human native angiostatin was deduced to be a plasminogen fragment including most of kringle 5 with the N-terminal sequence
Lys Val Tyr Leu Ser Glu Cys Lys Thr Gly [SEQ ID NO:1]
and the C-terminal sequence
Cys Tyr Thr Thr Asn Pro Arg [SEQ ID NO:4]
or
Cys Tyr Thr Thr Asn Pro Arg Lys [SEQ ID NO:5].

We claim:

1. A method of treating a malignant neoplastic disease comprising administering to a human suffering from said disease a therapeutically effective amount of plasminogen activator effective to increase the amount of angiostatin present in said human to treat the neoplastic disease.

2. The method of claim 1 further comprising administering a sulfhydryl donor selected from the group consisting of cysteine, N-acetyl cysteine, captopril, D-penicillamine and reduced glutathione.

3. The method of claim 1 wherein the plasminogen activator is selected from the group consisting of urokinase, streptokinase and tissue plasminogen activator.

4. The method of claim 2 wherein the plasminogen activator is selected from the group consisting of urokinase, streptokinase and tissue plasminogen activator.

5. The method of any one of claims 1–4 wherein the malignant neoplastic disease is a malignant tumor.

6. The method of claim 5 wherein the tumor has metastasized.

7. A method of treating a malignant neoplastic disease comprising administering to a human suffering from said disease a therapeutically effective amount of plasminogen activator and sulfhydryl donor effective to increase the amount of angiostatin present in said human to treat the neoplastic disease.

8. The method of claim 7 wherein the sulfhydryl donor is selected from the group consisting of cysteine, N-acetyl cysteine, captopril, D-penicillamine and reduced glutathione.

9. The method of claim 7 wherein the plasminogen activator is selected from the group consisting of urokinase, streptokinase and tissue plasminogen activator.

10. The method of claim 8 wherein the plasminogen activator is selected from the group consisting of urokinase, streptokinase and tissue plasminogen activator.

11. The method of any one of claims 7–10 wherein the malignant neoplastic disease is a malignant tumor.

12. The method of claim 11 wherein the tumor has metastasized.

13. The method of claims 1 or 7 further comprising administering plasminogen.

14. The method of claims 1 or 7 further comprising administering plasmin.

* * * * *